(12) United States Patent
Zhao et al.

(10) Patent No.: US 11,091,448 B2
(45) Date of Patent: *Aug. 17, 2021

(54) METHOD FOR PREPARING URATE TRANSPORTER 1 INHIBITOR

(71) Applicant: TIANJIN INSTITUTE OF PHARMACEUTICAL RESEARCH CO., LTD., Tianjin (CN)

(72) Inventors: Guilong Zhao, Tianjin (CN); Changying Liu, Tianjin (CN); Yuqiang Liu, Tianjin (CN); Huihui Chen, Tianjin (CN); Yuquan Li, Tianjin (CN); Haizhi Zhang, Tianjin (CN); Yafei Xie, Tianjin (CN); Jingwei Wu, Tianjin (CN); Wei Liu, Tianjin (CN); Weiren Xu, Tianjin (CN); Meixiang Zou, Tianjin (CN); Lida Tang, Tianjin (CN)

(73) Assignee: TIANJIN INSTITUTE OF PHARMACEUTICAL RESEARCH CO., LTD., Tianjin (CN)

( * ) Notice: Subject to any disclaimer, the term of this patent is extended or adjusted under 35 U.S.C. 154(b) by 11 days.

This patent is subject to a terminal disclaimer.

(21) Appl. No.: 16/312,164

(22) PCT Filed: Jun. 26, 2017

(86) PCT No.: PCT/CN2017/089993
§ 371 (c)(1),
(2) Date: Dec. 20, 2018

(87) PCT Pub. No.: WO2018/001197
PCT Pub. Date: Jan. 4, 2018

(65) Prior Publication Data
US 2019/0233381 A1    Aug. 1, 2019

(30) Foreign Application Priority Data
Jun. 29, 2016    (CN) .......................... 201610506171.0

(51) Int. Cl.
*C07D 249/12* (2006.01)
*C07D 249/08* (2006.01)
(Continued)

(52) U.S. Cl.
CPC ......... *C07D 249/12* (2013.01); *C07D 249/08* (2013.01)

(58) Field of Classification Search
CPC .... C07D 249/12; C07D 249/08; C07C 25/22; C07C 331/04; C07C 337/06
See application file for complete search history.

(56) References Cited

U.S. PATENT DOCUMENTS 10,584,104 B2*  3/2020  Zhao .................. A61K 31/4196
2018/0134670 A1*  5/2018  Zhao ........................ A61K 9/48

FOREIGN PATENT DOCUMENTS

| CN | 101348537 A | 1/2009 |
|---|---|---|
| CN | 107531649 A | 1/2018 |

(Continued)

OTHER PUBLICATIONS

U.S. Appl. No. 15/570,151, filed May 2018, Zhao, Guilong.*
(Continued)

*Primary Examiner* — Amanda L. Aguirre
(74) *Attorney, Agent, or Firm* — Edwin S. Flores; Daniel J. Chalker; Chalker Flores, LLP

(57) ABSTRACT

Provided is a method for preparing a URAT1 inhibitor, 2-((5-bromo-4-((4-bromonaphthalen-1-yl)methyl)-4H-1,2,4-triazol-3-yl)thio) acetic acid represented by the following formula ZXS-BR, the reaction equation of which being shown as follows. Compared with the prior art, the preparation method provided by the present application is of low cost, ease of handling, ease of quality control, and applicable to industrialization.

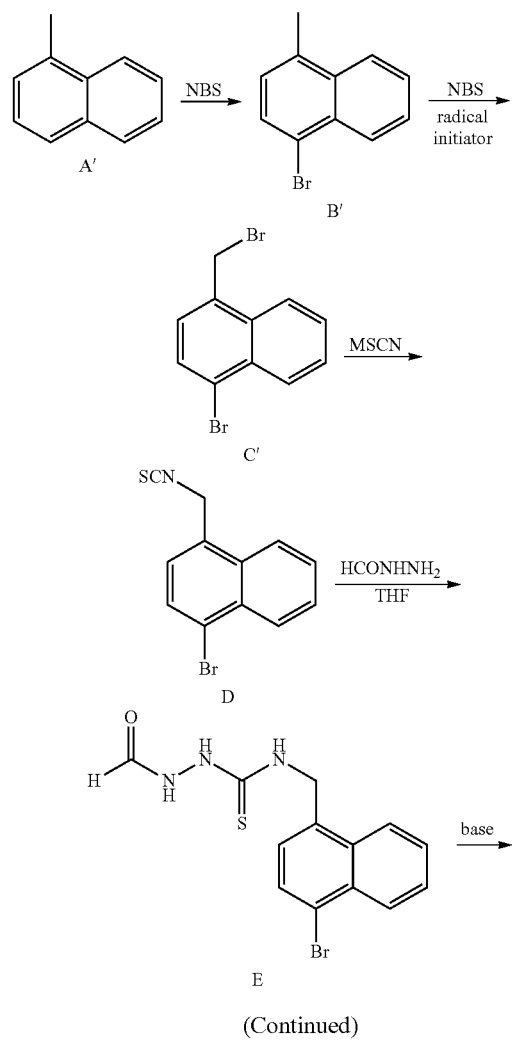

(Continued)

-continued

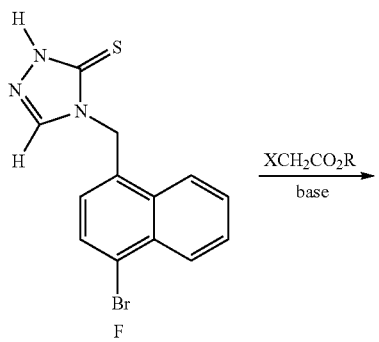

F

XCH₂CO₂R, base →

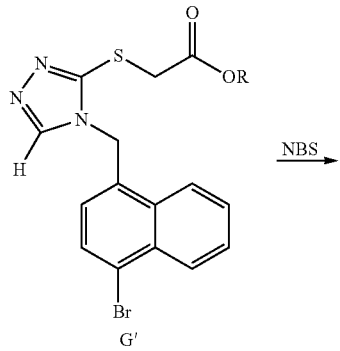

G'

NBS →

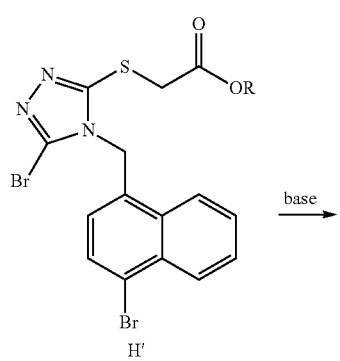

H' base →

-continued

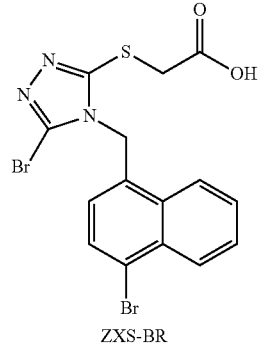

ZXS-BR

31 Claims, No Drawings

(51) Int. Cl.
C07C 331/04 (2006.01)
C07C 337/06 (2006.01)
C07C 25/22 (2006.01)

(56) References Cited

FOREIGN PATENT DOCUMENTS

WO 2010028190 A2 3/2010
WO 2016173503 A1 11/2016

OTHER PUBLICATIONS

Zhang et al. Medicinal Chemistry 2017, 13, 260-281. (Year: 2016).*
STN Database Registry No. 79996-99-9 [Entered STN: Nov. 16, 1984], (Year: 1984).*
Zhang et al. Phosphorus, Sulfur, and Silicon 2017, 192, 799-811 (pub. Feb. 2017). (Year: 2017).*
Zhang et al. Research Gate record for Medicinal Chemistry 2017, 13, 260-281 (pub. Sep. 2016). (Year: 2016).*
Horakova et al. "Cytotoxic and cancerostatic activity of isothiocyanates and related compounds. III. Effect of stilbene, azobenzene, and poly-condensed aromatic hydrocarbon isothiocyanate derivatives on HeLa cells" Neoplasma 1969, 16, 231-237. (Year: 1969).*
Chemical Abstract Service, STN Database, Registry No. 14570-46-8 [Entered STN: Nov. 16, 1984], (Year: 1984).*
Search Report CN201610561710 unknown date of report.
Moszew, Jan. "Synthetic plant-growth regulators. IX. Thiocyanates of the naphthalene series as potential plant-growth regulators" Zeszyty Naukowe Uniwersytetu Jagiellonskiego, Prace Chemiczne, (Dec. 31, 1964) p. 85, table I.
Yu, Xiaoqiang et al. "Cross-Coupling Reaction of Benzylic Halides with Allyltributylstannane Catalyzed by Cu(OTi)2". Chinese Journal of Catalysis. vol. 32, No. 3 (Dec. 31, 2011), p. 475, table 2.
International Search Report (PCT/CN2017/089993) [ISA/CN] dated Sep. 28, 2017.
European Search Report, EP 17819194.6 dated Nov. 27, 2019.
Boekelheide, V. et al.: "A Synthesis of 3-Bromoperinaphthanol-7", J Am Chem Soc, vol. 76, No. 2, 1953, pp. 604-605.
Tian, H. et al.: "Discovery of a Flexible Triazolylbutanoic Acid as a Highly Potent Uric Acid Transporter 1 (URAT1) Inhibitor", M0lecules, vol. 21, Nov. 16, 2016 (Nov. 16, 2016), p. 1543.
Zhang, X. et al.: "Discovery of Flexible Naphthyltriazolylmethane-Based Thioacetic Acid as Highly Active Uric Acid Transporter 1 (URAT1) Inhibitors for the Treatment of Hyperuricemia of Gout", Medicinal Chemistry, vol. 13, 2017, pp. 260-281.

* cited by examiner

METHOD FOR PREPARING URATE TRANSPORTER 1 INHIBITOR

CROSS-REFERENCE TO RELATED APPLICATIONS

This application is a National Stage of International Application No. PCT/CN2017/089993, filed Jun. 26, 2017, claiming the priority of CN2016105061710, filed on Jun. 29, 2016, the content of each of which is incorporated by reference herein.

TECHNICAL FIELD

The present invention belongs to pharmaceutical field. In particular, the present invention relates to a method for preparing a urate transporter 1 (URAT1) inhibitor, 2-((5-bromo-4-((4-bromonaphthalen-1-yl)methyl)-4H-1,2,4-triazol-3-yl)thio)acetic acid (ZXS-BR), which has a therapeutic effect on gout and hyperuricemia.

BACKGROUND ART

Gout is an inflammatory disease caused by deposition of monosodium urate (MSU) at joints and the surrounding tissues thereof, which is characterized by periodic joint swelling and pain. Without treatment, it could cause joint deformation and nephrolithiasis, even renal failure, and has serious impacts on the patients' life quality and health.

As a cause of gout attack, hyperuricemia is a disease state in which the concentration of serum uric acid (SUA) exceeds the solubility limit of uric acid (6.8 mg/dL, 404 μmol/L) in body fluid at physiological conditions (pH 7.4, temperature 37° C.). At physiological pH, 98% of uric acid is present in the form of ion. Because of the high concentration of extracellular $Na^+$, uric acid is mainly present in human body in the form of monosodium urate. Due to an evolutionary reason (uricase deficiency), urate is the end product of purine metabolism in human body. About one-third of urate produced by metabolism is excreted through gastrointestinal tract, and the remaining two-thirds are excreted through kidneys. There are two causes of hyperuricemia: one is too much urate produced, and the other is too little urate excreted through kidneys. About 10% of the patients with hyperuricemia produce too much urate, and 90% of the patients have too little urate excreted through kidneys. Sustained hyperuricemia can cause gout. In Europe and the United States, the incidence of hyperuricemia is about 20-30%, and the incidence of gout is about 3%; in China, the incidence of hyperuricemia is about 10%, and the incidence of gout is about 1%. The epidemiological surveys in recent years have shown that the incidences of both hyperuricemia and gout continue to rise.

Currently, drugs for the treatment of gout can be classified mainly into four types: the first type is anti-inflammatory analgesic drugs which can control the symptoms of acute gout attack, such as colchicine, steroidal anti-inflammatory drugs and nonsteroidal anti-inflammatory drugs; the second type is drugs that inhibit the production of urate, and thus can be used for the treatment of chronic gout and hyperuricemia, mainly including a xanthine oxidase inhibitor (XOI), such as allopurinol, febuxostat and topiroxosta; the third type is drugs that increase the excretion of urate, and thus can be used for the treatment of chronic gout and hyperuricemia, mainly including a urate transporter 1 (URAT1) inhibitor, such as probenecid, sulphinpyrazone, benzbromarone and the newly marketed lesinurad. Some drugs having special structures that are originally used for other indications also have effect on the excretion of urate, such as losartan for the treatment of hypertension and atorvastatin for the treatment of hyperlipidemia; the fourth type is uricase, which can be used to treat chronic gout that does not respond to traditional therapies or to reduce serum uric acid during an acute attack of gout.

There are many disadvantages in existing therapeutic drugs for gout. For example, some drugs have severe side effects. By way of example, colchicine, which is used to control an acute attack of gout, can cause diarrhea, vomiting, crampy abdominal pain and other common adverse effects, which are the first indications of its toxicity, with a therapeutically effective dose being close to the dose at which it causes gastrointestinal symptoms, and the incidence of side effects being extremely high (sometimes 100%). It had not been approved by the FDA in the United States until 2009. Other anti-inflammatory analgesic drugs to control an acute attack of gout can only control symptoms, but not ameliorate or treat gout itself. The clinical response rates of xanthine oxidase inhibitors are very low, most of which the effective rates are only about 40%-60%. In addition, allopurinol has severe allergic reactions, and the allergic reactions sometimes are lethal. Traditional drugs for the excretion of urate, such as probenecid, sulphinpyrazone and benzbromarone, also have many problems. Among them, probenecid has weak effect and poor selectivity (the inhibition strengths of URAT1, OAT1, OAT3 and OAT4 are similar); sulphinpyrazone and benzbromarone have severe side effects (the former inhibits platelets and bone marrow, and the latter has hepatotoxicity) and are not sold in the United States; benzbromarone was withdrawn from the market in Europe in 2003 and is now used in only a few countries; the disadvantages of newly approved lesinurad are weak efficacy and high dosage (200 mg), and the dosage for use and that causing side effects are very close to each other (obvious nephrolithiasis occurs at 400 mg, and renal failure is significantly aggravated compared to that at 200 mg); the disadvantage of uricase is that its use will result in generation of an antibody in human body (about 25% of patients will generate an antibody), resulting in a low efficiency (about 50%), a decreased efficacy during long-term use and infusion reactions. Therefore, it is of clinical value to develop a safe and effective therapeutic drug.

The urate in blood is filtered in glomerulus, and then about 90% is reabsorbed back into blood at renal proximal tubules. Urate transporter 1, which is responsible for the reabsorption, is a transporter discovered in 2002 (Enomoto A, Kimura H, Chairoungdua A, et al. Molecular identification of a renal urate anion exchanger that regulates blood urate levels. *Nature* 2002, 417 (6887), 447-452). A URAT1 inhibitor can reduce the concentration of serum urate by inhibiting the reabsorption of urate by URAT1 in kidneys so as to increase excretion of urate in urine, and thus can be used in the treatment of gout and hyperuricemia.

PCT/CN2016/080468 disclosed a URAT1 inhibitor, 2-((5-bromo-4-((4-bromonaphthalen-1-yl)methyl)-4H-1,2, 4-triazol-3-yl)thio)-acetic acid and a pharmaceutically acceptable salt thereof, which can be used in the treatment of gout and hyperuricemia (Example 51 of PCT/CN2016/080468, the structure of which is shown in the following formula; the compound is named "ZXS-BR" for convenience in the present invention). The URAT1 inhibitor has a strong in vitro inhibitory effect on URAT1-mediated uptake of $^{14}C$-urate by HEK293 cells, with $IC_{50}$ being 0.081 μM which is 88.6 times that of lesinurad (IC$_{50}$=7.18 μM), and it is applicable to preparation of a medicament for treating gout and hyperuricemia.

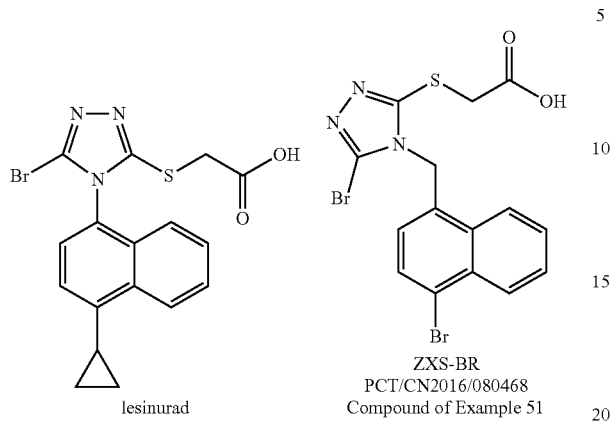

lesinurad

ZXS-BR
PCT/CN2016/080468
Compound of Example 51

PCT/CN2016/080468 also disclosed a method for the preparation of ZXS-BR as described above, i.e., a preparation process according to Example 1 in PCT/CN2016/080468 (see the description in the table included in Example 51, the third column of the first line). This process has the following disadvantages: starting material A (1,4-dibromonaphthalene) and the reagent thiophosgene are expensive; LiAlH$_4$ and thiophosgene are unfavorable for large-scale industrial production, because LiAlH$_4$ has a strong activity posing danger in feeding during the reaction and work-up, and thiophosgene has a strong unpleasant odor and is unfavourable for the health of operators; in the preparation of compound B by the reaction of compound A with CuCN, even in the reaction liquid obtained under the optimized reaction conditions, product B is accompanied with unreacted starting material A and the excessively cyanated by-product, 1,4-dicyanonaphthalene; moreover, the work-up of the reaction is complicated, and the yield of B is very low (Zhang Xiansheng, Liu Yuqiang et al, Synthesis Process Research of RDEA3170, Drugs & Clinic. 2015, 30(10), 1179-1184); a large amount of debromination product is always generated when compound B is reduced with LiAlH$_4$, resulting in a low final yield of B→F, and the presence of a debromination by-product and its transfer along the reaction route bring great uncertainty to the purification and quality control of intermediates C, D, F, and etc., and are unfavorable for large-scale industrial production.

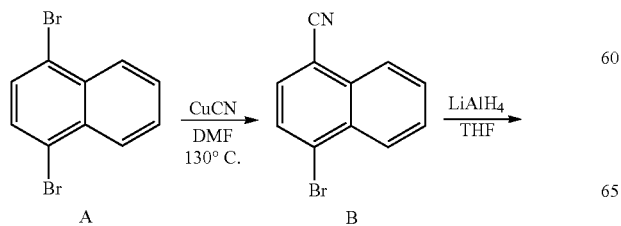

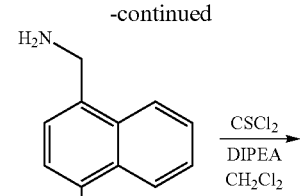

C

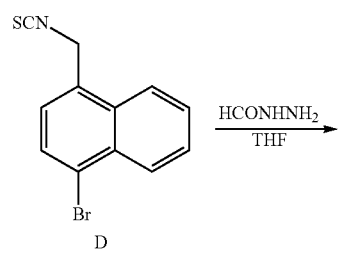

D

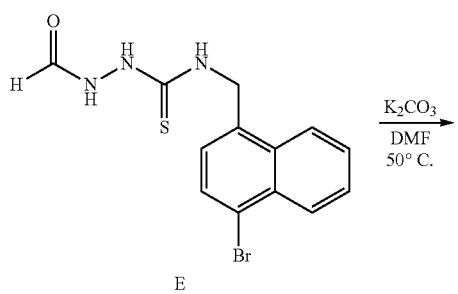

E

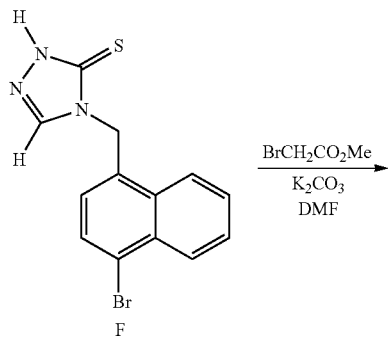

F

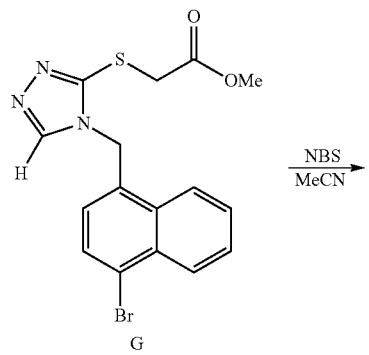

G

-continued

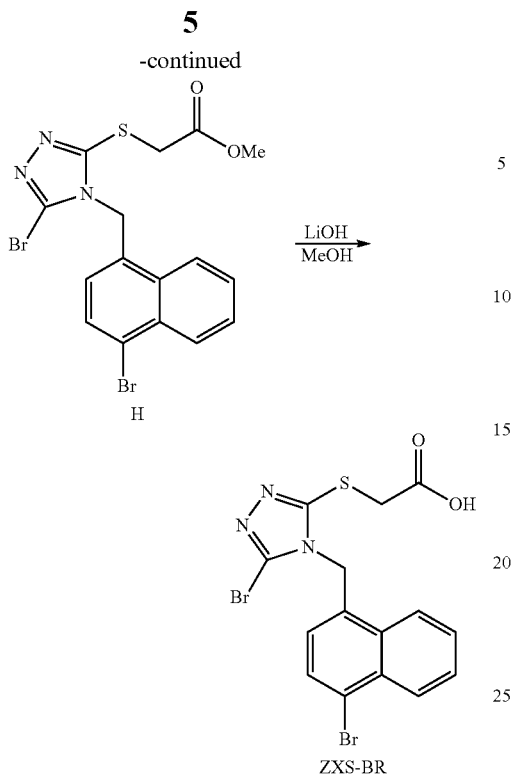

ZXS-BR

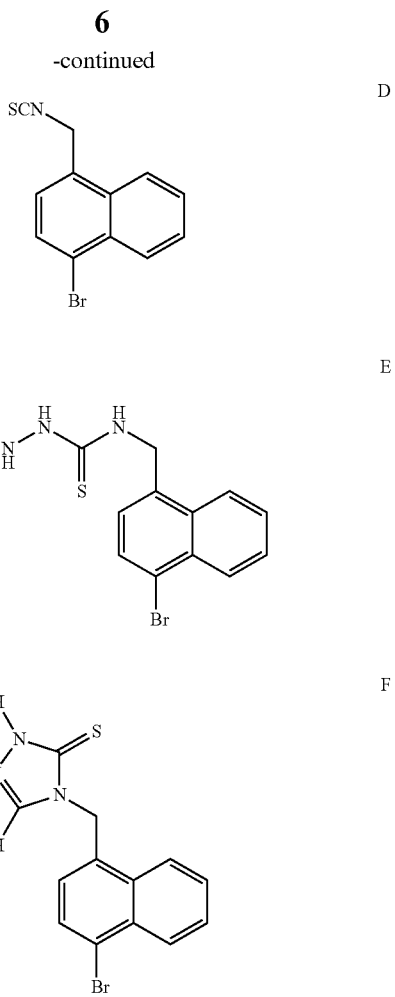

Content of the Invention

Accordingly, an object of the present invention is to overcome the disadvantages and deficiencies of the prior art and to provide a method for preparing a URAT1 inhibitor ZXS-BR, which is of low cost, ease of handling, ease of quality control, and applicable to a large-scale industrial operation.

In the present invention, unless otherwise specified, the formulas A', B', C', D, E, F, G', H' and ZXS-BR represent the compounds represented by the following formulas, respectively:

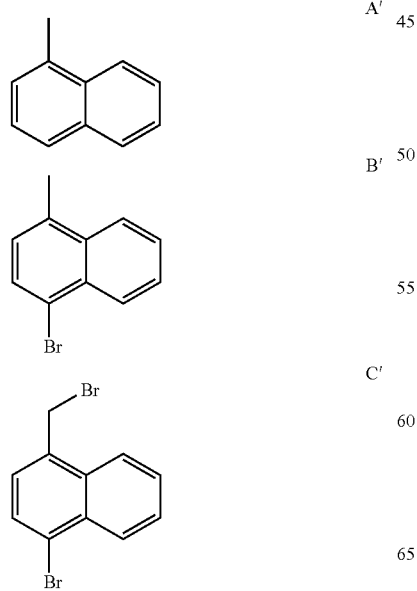

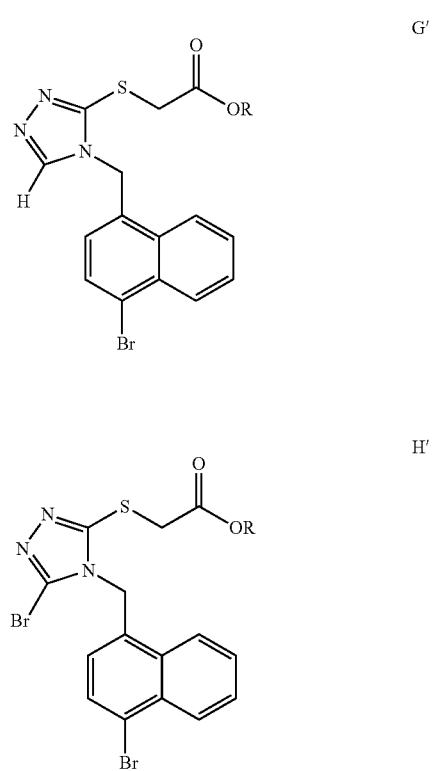

-continued

ZXS-BR

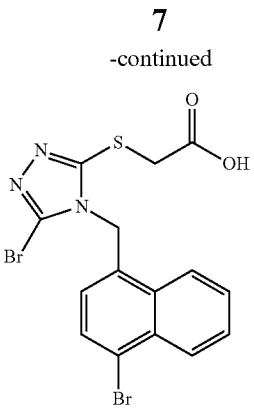

In one aspect, the invention provides a method for preparing a urate transporter 1 inhibitor, 2-((5-bromo-4-((4-bromonaphthalen-1-yl)methyl)-4H-1,2,4-triazol-3-yl)thio)acetic acid represented by the formula ZXS-BR, comprising the following steps:

1) performing a bromination reaction of N-bromosuccinimide (NBS) and starting material A' (1-methylnaphthalene) to obtain product B';

preferably, the solvent of the reaction is acetonitrile (MeCN), and the reaction temperature is from 30 to 40° C.;

2) reacting product B' obtained from step 1) with N-bromosuccinimide in the presence of a radical initiator to obtain product C';

wherein, the radical initiator is benzoyl peroxide (BPO) or azodiisobutyronitrile (AIBN);

preferably, the solvent of the reaction is selected from $C_5$-$C_{17}$ alkane or cycloalkane, or a petroleum ether fraction at 30-150° C.; more preferably, $C_5$-$C_{17}$ alkane or cycloalkane is n-pentane, cyclopentane, n-hexane, cyclohexane or n-heptane;

preferably, the temperature of the reaction is from 36° C. to 120° C.; more preferably, the temperature of the reaction is the reflux temperature of the solvent;

3) reacting product C' obtained from step 2) with a thiocyanate (MSCN) at a temperature no lower than 100° C. to obtain product D;

wherein, the thiocyanate is a thiocyanate of alkali metal, alkaline earth metal or ammonium; preferably, the thiocyanate is sodium thiocyanate, potassium thiocyanate, or ammonium thiocyanate;

preferably, the solvent of the reaction is an aprotic dipolar solvent; more preferably, the aprotic dipolar solvent is selected from dimethylformamide (DMF), N,N-dimethylacetamide (DMA), dimethyl sulfoxide (DMSO), N-methylpyrrolidone (NMP), or hexamethylphosphoramide (HMPA);

preferably, the temperature of the reaction is from 100° C. to the reflux temperature of the solvent; more preferably, the temperature of the reaction is from 120° C. to 140° C.;

4) reacting product D obtained from step 3) with formylhydrazine to obtain product E;

preferably, the solvent of the reaction is tetrahydrofuran (THF);

5) performing a ring closure reaction of product E obtained from step 4) in the presence of a base to obtain product F;

preferably, the base is an alkali metal carbonate or an alkali metal hydroxide, more preferably, $Na_2CO_3$, $K_2CO_3$, NaOH or KOH;

6) reacting product F obtained from step 5) with $XCH_2CO_2R$ in the presence of a base to obtain product G';

wherein, X is selected from Cl, Br or I, R is selected from $C_1$-$C_{10}$ alkyl or $C_3$-$C_6$ cycloalkyl; preferably, R is selected from $C_1$-$C_4$ alkyl; more preferably, R is selected from methyl or ethyl;

7) reacting product G' obtained from step 6) with NBS to obtain product H'

8) hydrolyzing product H' obtained from step 7) in the presence of a base to obtain ZXS-BR;

preferably, the base is selected from an alkali metal hydroxide; more preferably, the base is selected from LiOH, NaOH or KOH.

The reaction equation for the above preparation method is shown below:

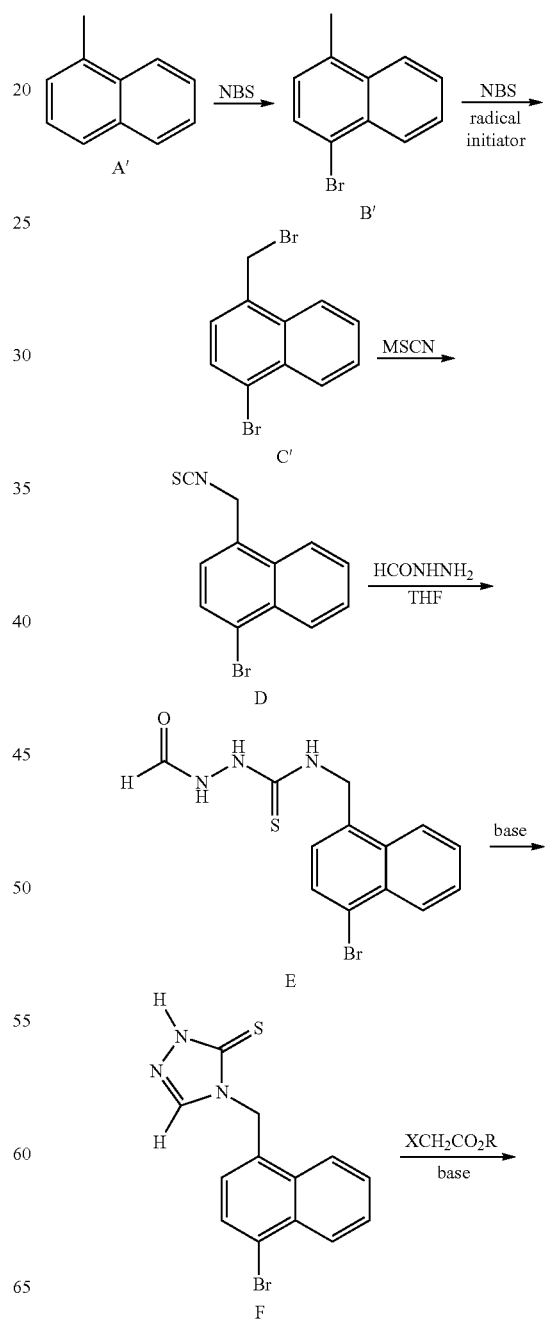

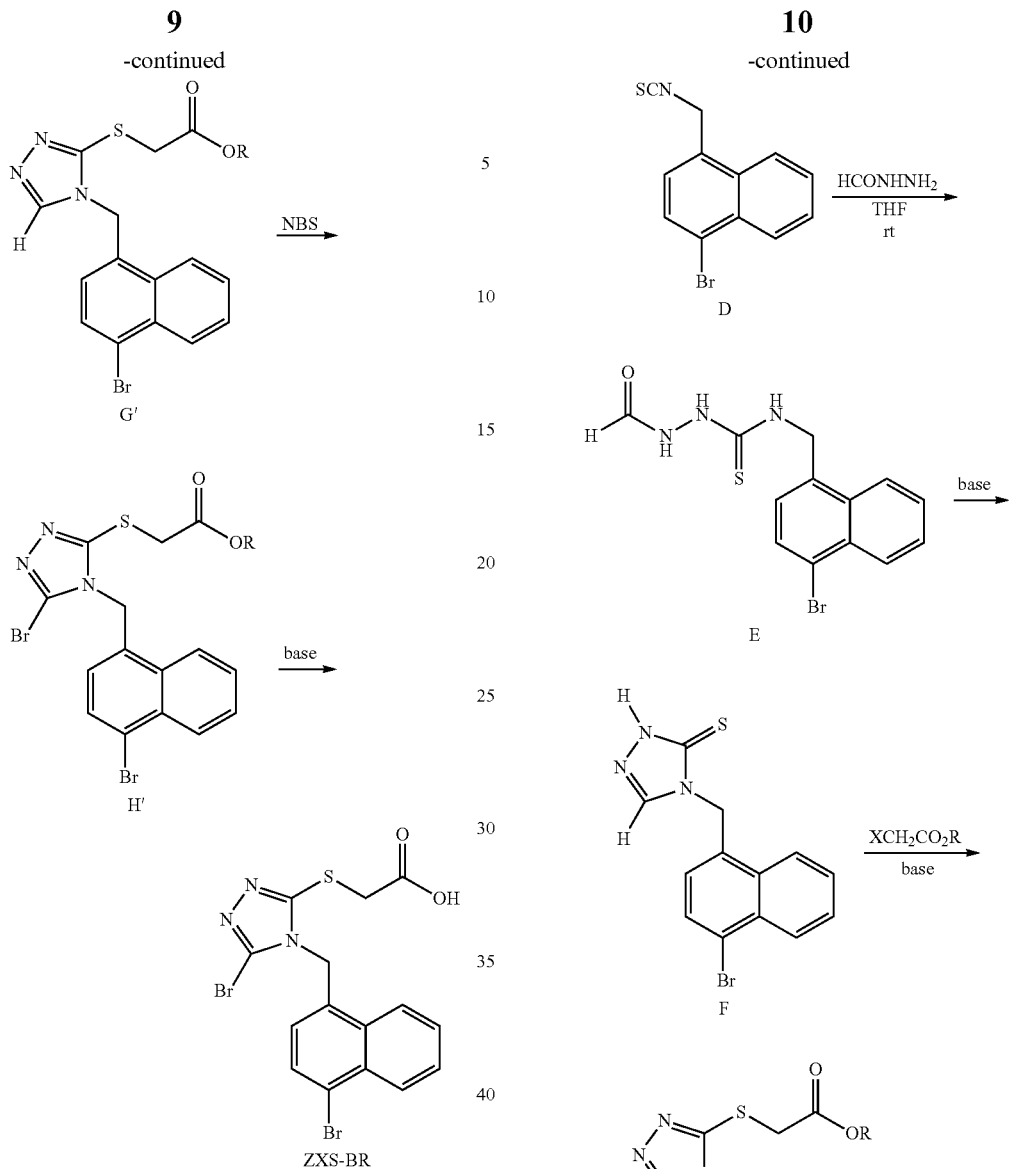
In a preferred embodiment, the reaction equation for the preparation method is shown below:
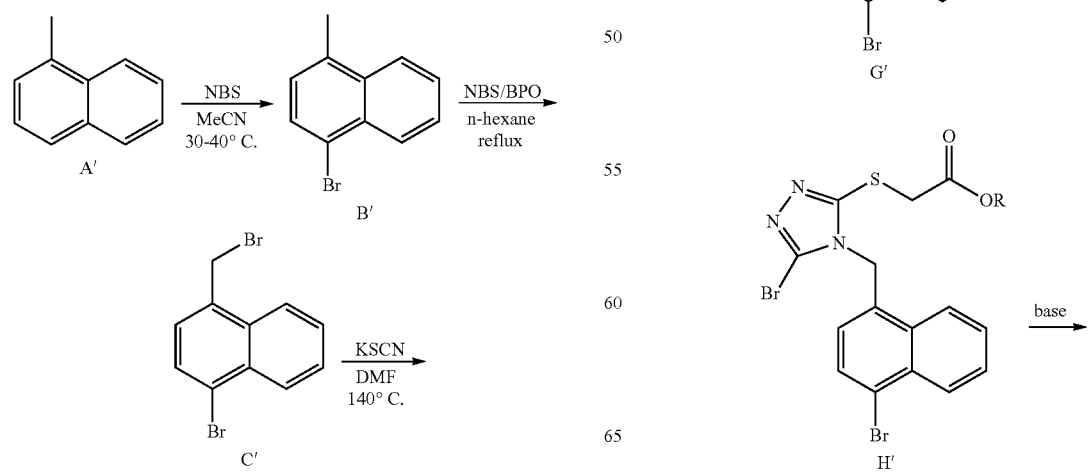

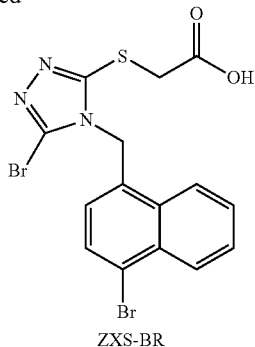

ZXS-BR wherein, the method comprises the following steps:

1) brominating starting material A' (1-methylnaphthalene) with N-bromosuccinimide (NBS) in MeCN as a solvent at a temperature of 30-40° C. to obtain product B';

2) heating product B' obtained from step 1), NBS and BPO in n-hexane to reflux to obtain product C';

3) reacting product C' obtained from step 2) with KSCN in DMF as a solvent at a temperature of 140° C. to obtain product D;

4) reacting product D obtained from step 3) with formylhydrazine in THF as a solvent at room temperature to obtain product E;

5) performing a ring closure reaction of product E obtained from step 4) with a base to obtain product F;

preferably, the base is an alkali metal carbonate or an alkali metal hydroxide, more preferably, $Na_2CO_3$, $K_2CO_3$, NaOH or KOH;

6) reacting product F obtained from step 5) with $XCH_2CO_2R$ in the presence of a base to obtain product G';

wherein, X is selected from Cl, Br or I, R is selected from $C_1$-$C_{10}$ alkyl or $C_3$-$C_6$ cycloalkyl;

preferably, R is selected from $C_1$-$C_4$ alkyl;

more preferably, R is selected from methyl or ethyl;

7) reacting product G' obtained from step 6) with NBS to obtain product H'

8) hydrolyzing product H' obtained from step 7) with a base to obtain ZXS-BR;

preferably, the base is an alkali metal hydroxide;

more preferably, the base is LiOH, NaOH or KOH.

In another aspect, the present invention also provides a compound represented by the following formula H':

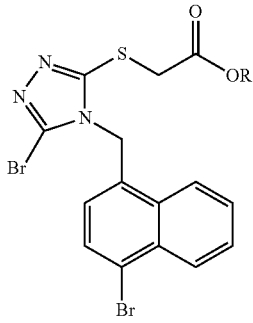

H' wherein, R is selected from $C_1$-$C_{10}$ alkyl or $C_3$-$C_6$ cycloalkyl; preferably, R is selected from $C_1$-$C_4$ alkyl; more preferably, R is selected from methyl or ethyl.

In another aspect, the present invention also provides a compound represented by the following formula G':

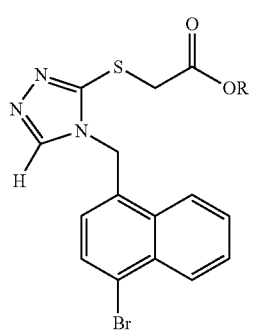

G' wherein, R is selected from $C_1$-$C_{10}$ alkyl or $C_3$-$C_6$ cycloalkyl; preferably, R is selected from $C_1$-$C_4$ alkyl; more preferably, R is selected from methyl or ethyl.

In still another aspect, the present invention also provides the compounds represented by the following formulas C', D, E, and F, respectively:

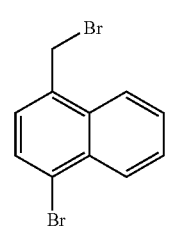

C'

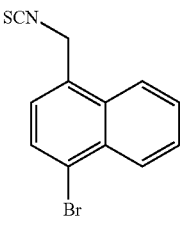

D

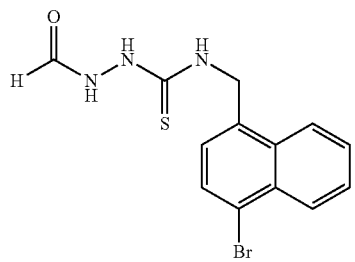

E

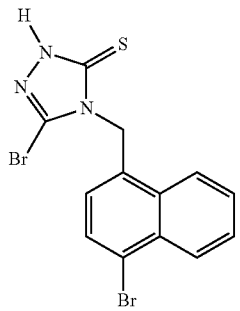

F

Compared with the prior art, the preparation method provided by the present application has the following advantages:

1) starting material A' (1-methylnaphthalene) is inexpensive, resulting a significant decrease in cost as compared with that of A (1,4-dibromonaphthalene) in the prior process;
2) there are no expensive reagents;
3) there are no hazardous reagents such as LiAlH$_4$, thiophosgene, and etc, which are unfavorable for large-scale industrial production, and therefore it is easier for handling and quality control;
4) the reaction yield of A'→B'→C'→D is high, and there is no unfavorable reaction factors such as A→B, B→C and etc, resulting in a low yield and difficulties in quality control of the intermediates in a similar prior process.

In summary, the preparation method provided by the present invention is of low cost, ease of handling, ease of quality control, and applicable to industrialization as compared with the prior art.

BEST MODE FOR CARRYING OUT THE INVENTION

The present invention will be further described in detail in connection with the specific embodiments thereof. The examples are given only to illustrate the invention and not intended to limit the scope of the invention.

Example 1 Synthetic Route of PCT/CN2016/080468

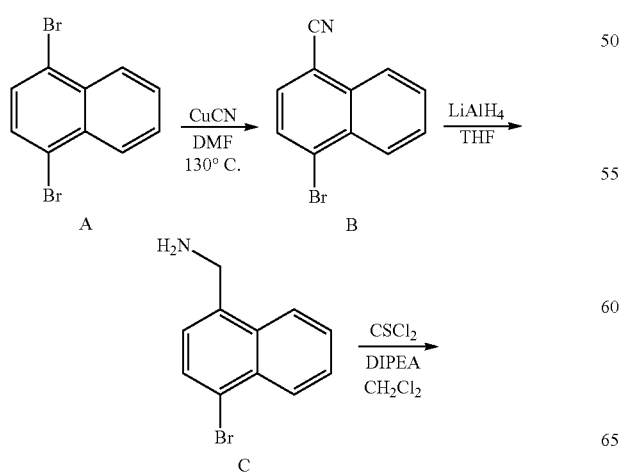

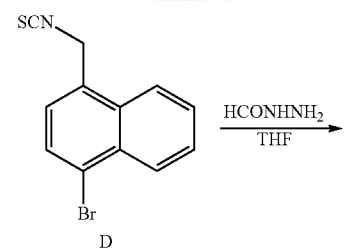

D

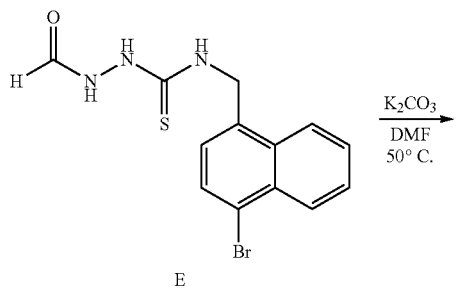

E

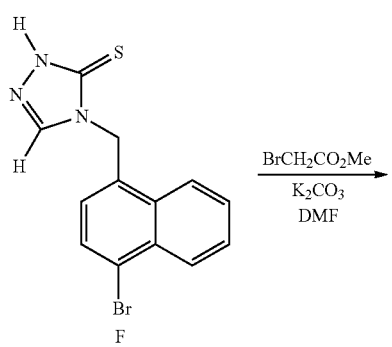

F

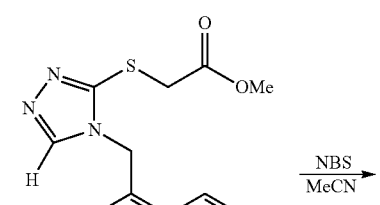

G

H

-continued

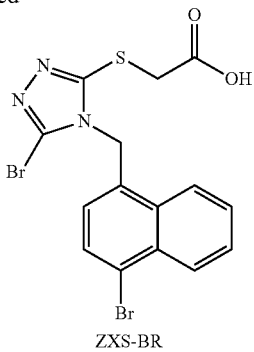

ZXS-BR

Step 1. Synthesis of Compound B

To a dry 1 L round bottom flask were added compound A (1,4-dibromonaphthalene, 57.19 g, 200 mmol), CuCN (10.75 g, 120 mmol) and DMF (600 mL), and the resulting mixture was stirred at 130° C. under nitrogen atmosphere for 12 hours.

The reaction mixture was cooled to room temperature and transferred to a 5 L flask. Ethyl acetate (1.8 L) was added, and the resulting mixture was stirred at room temperature for 2-3 hours to give a grayish brown slurry. The slurry was filtered by suction, and the filtrate was collected. The filter cake was washed with a small amount of ethyl acetate, and the washing liquid was combined into the filtrate. The filtrate was washed with water (1 L×5), dried over anhydrous sodium sulfate, and evaporated on a rotary evaporator to remove the solvent. To the resulting yellow solid was added ethyl acetate-petroleum ether (400 mL, a volume ratio of 1:3), and the resulting mixture was warmed to 70° C. and stirred to give a clear solution. After the solution was cooled slowly with stirring to room temperature, a yellow slurry was obtained. The slurry was filtered by suction, the filtrate was collected which was evaporated to dryness on a rotary evaporator, and the resulting residue was purified by silica gel column chromatography, and eluted with ethyl acetate-petroleum ether (1:50→1:30) to obtain a pure product of B as a white solid, 12.53 g; yield: 27%; m.p.: 103-104° C.; $^1$H NMR (DMSO-$d_6$, 400 MHz), δ 8.26-8.31 (m, 1H, Ar—H), 8.13-8.18 (m, 1H, Ar—H), 8.07 (s, 2H, Ar—H), 7.85-7.92 (m, 3H, Ar—H).

Step 2. Synthesis of Compound C

Compound B (11.60 g, 50 mmol) was dissolved in dry THF (200 mL) and stirred, and LiAlH$_4$ (2.77 g, 73 mmol) was added slowly in portions with cooling in an ice-water bath. After completion of the addition, the reaction mixture was stirred in the ice-water bath for another 2 hours.

The reaction mixture was carefully and slowly poured into stirring ice water (400 mL), stirred, and extracted with CH$_2$Cl$_2$ (200 mL×3). The extracted organic phases were combined, washed with 5% saline solution (200 mL), and dried over anhydrous Na$_2$SO$_4$. The dried organic phase was evaporated on a rotary evaporator to remove the solvent, and the resulting residue was purified by column chromatography to give product C as a colorless oil. $^1$H NMR showed that about 30% debromination by-product (i.e., naphthalene-1-methylamine) was contained therein and a further purification was difficult, and therefore the mixture was used for the next reaction directly.

Step 3. Synthesis of Compound D

The crude compound C (calculated as 50 mmol) prepared in the above step 2 and diisopropylethylamine (DIPEA, 19.39 g, 150 mmol) were dissolved in dry CH$_2$Cl$_2$ (200 mL), and the resulting solution was stirred with cooling in an ice-water bath. Then CSCl$_2$ (6.90 g, 60 mmol) was slowly added dropwise, and after the dropwise addition was completed, the resulting solution was stirred at room temperature for another 1 hour. At this point the reaction was checked for completion by TLC.

The reaction mixture was carefully and slowly poured into stirring ice water (400 mL) and stirred, the organic phase was separated, and the aqueous phase was extracted with CH$_2$Cl$_2$ (150 mL×2). The organic phases were combined, washed with 2% dilute hydrochloric acid (300 mL) and 5% saline solution (200 mL) sequentially, and dried over anhydrous Na$_2$SO$_4$. The dried organic phase was evaporated on a rotary evaporator to remove the solvent, and the resulting residue was purified by column chromatography to give product D as a white solid, 8.21 g; yield: 59%. $^1$H NMR showed that about 8% debromination by-product was contained therein and a further purification was difficult, and therefore the residue was used for the next reaction directly. A small amount of the above-described crude D was subjected to three column chromatographies and two recrystallizations consecutively to give a sample of pure product D as a white solid for structural characterization; m.p.: 94.5-97.5° C. $^1$H NM R (DMSO-$d_6$, 400 MHz), δ 8.21-8.24 (m, 1H), 8.11-8.14 (m, 1H), 7.92 (d, 1H, J=7.6 Hz), 7.73-7.78 (m, 2H), 7.52 (d, 1H, J=8.0 Hz), 5.41 (s, 2H).

Step 4. Synthesis of Compound F

The above-described crude compound D (6.95 g, calculated as 25 mmol) was dissolved in THF (100 mL), and stirred at room temperature. Formylhydrazine (1.80 g, 30 mmol) was added, and then the stirring was continued overnight. At this point the reaction was detected for completion by TLC.

The reaction mixture was evaporated on a rotary evaporator to dryness, the resulting residue, i.e., a crude product of E, was dissolved in DMF (80 mL), and solid K$_2$CO$_3$ (3.46 g, 25 mol) was added. The reaction mixture was stirred at 50° C. until the reaction was completed (usually 5 hours).

The reaction mixture was cooled to room temperature, poured into ice water (400 mL), stirred, adjusted with hydrochloric acid to pH=5-6, and extracted with CH$_2$Cl$_2$ (150 mL×5). The organic phases were combined, washed with 5% saline solution (200 mL), and dried over anhydrous Na$_2$SO$_4$. The dried organic phase was evaporated on a rotary evaporator to remove the solvent, and the resulting residue was purified by column chromatography to give product F as a white solid. $^1$H NMR showed that about 5% debromination by-product was contained therein. The crude F was crystallized twice with ethyl acetate to give a pure product of F, 6.96 g; yield: 87% (D→F); m.p.: 243-244° C. $^1$H NMR (DMSO-$d_6$, 400 MHz), δ 13.88 (brs, 1H), 8.37 (s, 1H), 8.22 (d, 2H, J=7.6 Hz), 7.90 (d, 1H, J=7.2 Hz), 7.72 (m, 2H), 7.18 (d, 1H, J=7.2 Hz), 5.61 (s, 2H).

Step 5. Synthesis of Compound G

Compound F (6.40 g, 20 mmol) was dissolved in DMF (100 mL) and stirred at room temperature, and solid K$_2$CO$_3$ (8.29 g, 60 mmol) and methyl bromoacetate (3.67 g, 24 mmol) were added. The resulting reaction mixture was stirred continuously at room temperature until the completion of the reaction was found by TLC determination (usually within 5 hours).

The reaction mixture was poured into ice water (400 mL), stirred, and extracted with CH$_2$Cl$_2$ (100 mL×5). The organic phases were combined, washed with 5% saline solution (200 mL), and dried over anhydrous Na$_2$SO$_4$. The dried organic phase was evaporated on a rotary evaporator to remove the solvent, and the resulting residue was purified by column chromatography to give product G as a white solid, 7.37 g; yield: 94%; m.p.: 112.5-114° C. $^1$H NMR (DMSO-d$_6$, 400 MHz), δ 8.67 (s, 1H), 8.22-8.25 (m, 1H), 8.15-8.17 (m, 1H), 7.88 (d, 1H, J=7.6 Hz), 7.72-7.79 (m, 2H), 6.92 (d, 1H, J=7.6 Hz), 5.72 (s, 2H), 4.07 (s, 2H), 3.62 (s, 3H).

Step 6. Synthesis of Compound H

Compound G (3.92 g, 10 mmol) was dissolved in acetonitrile (50 mL) and stirred at room temperature. NBS (2.14 g, 12 mmol) was added, and the stirring was continued at room temperature until the completion of the reaction was found by TLC determination (usually within 12 hours).

The reaction mixture was poured into ice water (200 mL), stirred, and extracted with CH$_2$Cl$_2$ (100 mL×3). The organic phases were combined, and washed with a saturated Na$_2$CO$_3$ solution (100 mL×3) and 5% saline solution (200 mL) sequentially, and dried over anhydrous Na$_2$SO$_4$. The dried organic phase was evaporated on a rotary evaporator to remove the solvent, and the resulting residue was purified by column chromatography to give product H as a white solid, 3.49 g; m.p.: 141-143° C.; yield: 74%. $^1$H NMR (DMSO-d$_6$, 400 MHz), δ 8.21-8.26 (m, 2H), 7.84 (d, 1H, J=8.0 Hz), 7.76-7.82 (m, 2H), 6.49 (d, 1H, J=7.6 Hz), 5.74 (s, 2H), 4.08 (s, 2H), 3.61 (s, 3H).

Step 7. Synthesis of ZXS-BR

Compound H (3.30 g, 7 mmol) was added into methanol (50 mL) and stirred at room temperature. A solution made by LiOH.H$_2$O (0.84 g, 20 mmol) and water (3 mL) was added, and then stirred at room temperature until the completion of the reaction was found by TLC determination (usually 2 hours).

The reaction mixture was poured into ice water (200 mL), stirred, adjusted with hydrochloric acid to pH=2-3, and extracted with CH$_2$Cl$_2$ (100 mL×4). The organic phases were combined, washed with 5% saline solution (200 mL), and dried over anhydrous Na$_2$SO$_4$. The dried organic phase was evaporated on a rotary evaporator to remove the solvent, and the resulting residue was purified by column chromatography to give product ZXS-BR as a white solid, 2.82 g; yield: 88%; m.p.: 169.5-171.5° C. $^1$H NMR (DMSO-d$_6$, 400 MHz), δ 12.97 (brs, 1H), 8.22-8.26 (m, 2H), 7.83 (d, 1H, J=8.0 Hz), 7.76-7.81 (m, 2H), 6.51 (d, 1H, J=8.0 Hz), 5.73 (s, 2H), 4.01 (s, 2H).

Example 2 Screening Study on Reaction Conditions in the Step of B'→C'

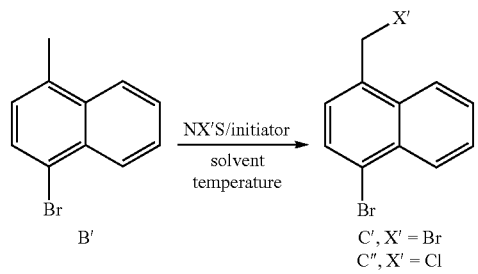

It is recognized by one of ordinary skill in the art that free radical halogenation at the benzylic position of an aralkyl group is generally carried out by heating in a solvent such as CCl$_4$ with NBS (N-bromosuccinimide) or NCS (N-chlorosuccinimide) as a halogenating agent, BPO or azodiisobutyronitrile (AIBN) and the like as a radical initiator. However, the inventors of the present invention had found that the reaction proceeds unsmoothly in a solvent recognized by a person skilled in the art such as CCl$_4$, and thus carried out a intensive and delicate optimization and screening of the main reaction conditions of the reaction, that is, the halogenating agent, the radical initiator and the reaction solvent, and finally found that n-hexane is the most appropriate solvent, BPO is the optimal radical initiator, and NBS is the best halogenating reagent for this reaction.

Reaction operations: to a dry 250 mL round bottom flask was added a solvent to be screened (40 mL) at room temperature. B' (3.54 g, 16 mmol), a radical initiator (0.32 mmol), and NBS or NCS (19.2 mmol) was added with stirring, and warmed to an indicated temperature while stirring, and the reaction was monitored by TLC. After the reaction started, 0.32 mmol radical initiator was added once every 8 hours, until TLC showed that the reaction was self-terminated (B' disappeared) or aborted (no reaction occurred after 72 hours). If no reaction was found by TLC, or C'/C" was not generated, the reaction did not need to be treated; if C'/C" was generated, the reaction was processed in accordance with the following steps: after the reaction was completed, the system was cooled to room temperature, and the reaction mixture was concentrated to ⅓ volume on a rotary evaporator, poured into water (200 mL), stirred, and extracted with CH$_2$Cl$_2$ (50 mL×3). The extract phases were combined, washed with a saturated NaHCO$_3$ solution (50 mL×3) and 5% saline solution (50 mL) sequentially, dried over anhydrous Na$_2$SO$_4$ and filtered by suction to remove the desiccant. Then the filtrate was evaporated to dryness on a rotary evaporator, and the residue was purified by column chromatography to give a pure product of C'/C". The yields are calculated, and the reaction conditions and the results are shown in Table 1.

TABLE 1

| | | Reaction conditions and results | | | |
|---|---|---|---|---|---|
| Experiment No. | Halogenating reagent | Radical initiator | Solvent | Reaction temperature* | Conclusion |
| 1 | NBS | BPO | CCl$_4$ | reflux temperature of CCl$_4$ | raw material B' disappeared, the yield of C' was 8% |
| 2 | NBS | BPO | CHCl$_3$ | reflux temperature of CHCl$_3$ | raw material B' disappeared, the yield of C' was 2% |

TABLE 1-continued

Reaction conditions and results

| Experiment No. | Halogenating reagent | Radical initiator | Solvent | Reaction temperature* | Conclusion |
|---|---|---|---|---|---|
| 3 | NBS | BPO | CH$_2$Cl$_2$ | reflux temperature of CH$_2$Cl$_2$ | raw material B' did not react within 72 hours |
| 4 | NBS | BPO | acetone | reflux temperature of acetone | raw material B' disappeared, the yield of C' was 0% |
| 5 | NBS | BPO | DMF | 100° C. | raw material B' disappeared, the yield of C' was 0% |
| 6 | NBS | BPO | MeCN | reflux temperature of MeCN | raw material B' disappeared, the yield of C' was 0% |
| 7 | NBS | AIBN | MeCN | reflux temperature of MeCN | raw material B' disappeared, the yield of C' was 4% |
| 8 | NBS | BPO | THF | reflux temperature of THF | raw material B' disappeared, the yield of C' was 0% |
| 9 | NBS | AIBN | THF | reflux temperature of THF | raw material B' disappeared, the yield of C' was 6% |
| 10 | NBS | BPO | n-hexane | reflux temperature of n-hexane | raw material B' disappeared, the yield of C' was 72% |
| 11 | NBS | AIBN | n-hexane | reflux temperature of n-hexane | raw material B' disappeared, the yield of C' was 41% |
| 12 | NBS | BPO | cyclohexane | reflux temperature of cyclohexane | raw material B' disappeared, the yield of C' was 67% |
| 13 | NBS | BPO | n-pentane | reflux temperature of n-pentane | raw material B' disappeared, the yield of C' was 61% |
| 14 | NBS | BPO | cyclopentane | reflux temperature of cyclopentane | raw material B' disappeared, the yield of C' was 69% |
| 15 | NBS | BPO | n-heptane | 70-80° C. | raw material B' disappeared, the yield of C' was 62% |
| 16 | NBS | BPO | cycloheptane | 70-80° C. | raw material B' disappeared, the yield of C' was 54% |
| 17 | NBS | BPO | n-heptane | reflux temperature of n-heptane | raw material B' disappeared, the yield of C' was 61% |
| 18 | NBS | BPO | cycloheptane | reflux temperature of cycloheptane | raw material B' disappeared, the yield of C' was 55% |
| 19 | NBS | BPO | n-octane | 70-80° C. | raw material B' disappeared, the yield of C' was 64% |
| 20 | NBS | BPO | n-nonane | 70-80° C. | raw material B' disappeared, the yield of C' was 59% |
| 21 | NBS | BPO | n-decane | 70-80° C. | raw material B' disappeared, the yield of C' was 58% |
| 22 | NBS | BPO | n-undecane | 70-80° C. | raw material B' disappeared, the yield of C' was 67% |
| 23 | NBS | BPO | n-dodecane | 70-80° C. | raw material B' disappeared, the yield of C' was 51% |
| 24 | NBS | BPO | n-tridecane | 70-80° C. | raw material B' disappeared, the yield of C' was 59% |
| 25 | NBS | BPO | n-tetradecane | 70-80° C. | raw material B' disappeared, the yield of C' was 55% |
| 26 | NBS | BPO | n-pentadecane | 70-80° C. | raw material B' disappeared, the yield of C' was 61% |
| 27 | NBS | BPO | n-hexadecane | 70-80° C. | raw material B' disappeared, the yield of C' was 62% |

TABLE 1-continued

Reaction conditions and results

| Experiment No. | Halogenating reagent | Radical initiator | Solvent | Reaction temperature* | Conclusion |
|---|---|---|---|---|---|
| 28 | NBS | BPO | n-heptadecane | 70-80° C. | raw material B' disappeared, the yield of C' was 63% |
| 29 | NBS | BPO | petroleum ether fraction at 30-60° C. | reflux temperature | raw material B' disappeared, the yield of C' was 53% |
| 30 | NBS | BPO | petroleum ether fraction at 60-90° C. | reflux temperature | raw material B' disappeared, the yield of C' was 56% |
| 31 | NBS | BPO | petroleum ether fraction at 90-120° C. | 70-80° C. | raw material B' disappeared, the yield of C' was 53% |
| 32 | NBS | BPO | petroleum ether fraction at 120-150° C. | 70-80° C. | raw material B' disappeared, the yield of C' was 55% |
| 33 | NCS | BPO | n-hexane | reflux temperature of n-hexane | most of raw material B' was recovered, the yield of C'' was 9% |

*Note:
the boiling temperature of a solvent under a pressure of 760 mmHg is the boiling point of the solvent, but it is a common knowledge of those of ordinary skill in the art that under actual experimental conditions, the actual boiling temperature of a solvent is affected by many factors (such as the altitude of experiment site and the types and concentrations of solutes dissolved in the solvent) and may fluctuate around its standard boiling point. The actual reflux temperatures of several solvents described in the above table are also around their boiling points. The boiling point of $CCl_4$ is 76.8° C.; the boiling point of $CHCl_3$ is 61° C.; the boiling point of $CH_2Cl_2$ is 39.8° C.; the boiling point of acetone is 56.5° C.; the boiling point of MeCN is 81° C.; the boiling point of THF is 65° C.; the boiling point of n-hexane is 69° C.; the boiling point of cyclohexaneis 80° C.; the boiling point of n-pentane is 36° C.; the boiling point of cyclopentane is 49° C.; the boiling point of n-heptane is 98.5° C.; the boiling point of cycloheptane is 118.5° C. (a reasonable moderate reflux rate was achieved at about 120° C. in this experiment); petroleum ether fraction at 30-60° C. is moderately refluxed at about 35° C.; petroleum ether fraction at 60-90° C. is moderately refluxed at about 65° C.; petroleum ether fraction at 90-120° C. is moderately refluxed at about 95° C.; and petroleum ether fraction at 120-150° C. is moderately reflaxed at about 125° C.

Conclusion: as can be seen from Table 1, NBS is the optimal halogenating reagent in this step, and the reaction is too slow when using NCS; the optimal initiator is BPO, and the effect of AIBN is average; among all solvents to be tested, $C_5$-$C_{17}$ alkane and cycloalkane and petroleum ether fraction at 30-150° C. are optimal; and the reaction temperature is in a range of from about 36° C. (the reflux temperature of n-pentane) to 120° C. (the reflux temperature of cycloheptane).

Example 3 Screening Study on Reaction Temperature in the Step of C' to D

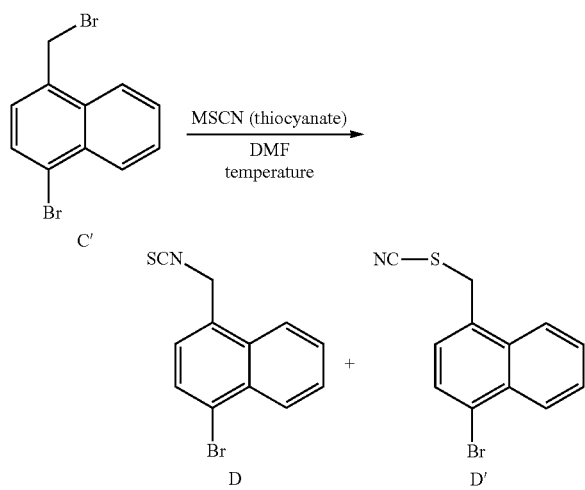

It is recognized by one of ordinary skill in the art that the reaction of an aromatic benzyl halide with a thiocyanate is relatively easy. Since the reaction can generally be carried out at a lower temperature, there is generally no motivation to operate at a higher temperature (for the sake of saving energy and power consumption). Therefore, when trying to react C' with KSCN in DMF at room temperature, we found that the reaction was very rapid (completed within 0.5 hours), and a single product was obtained. But after separation and structural identification, it was found that the product was not the desired D (an isothiocyanate), but its isomer D' (a thiocyanate), with the latter being a product of the reaction of S-terminal of thiocyanate ion in KSCN with C'. To this end, we carried out a detailed and intensive study on the types of thiocyanate and the temperatures of the reaction, and finally found that the reaction needed to be carried out within a specific range of higher temperatures so as to ensure the selectivity of N-terminal of thiocyanate ion to C' in the reaction.

Reaction operations: to a dry 250 mL round bottom flask was added compound C' (3.00 g, 10 mmol), which was dissolved in a dry solvent (30 mL), and then warmed to an indicated temperature with stirring. A thiocyanate MSCN (12 mmol) was added in three portions within 1 minute. After the addition was completed, the reaction mixture was further stirred at the indicated temperature for 1 hour, and at this point the reaction was completed. The reaction mixture was cooled to room temperature, and then poured into stirring ice water (200 mL), stirred and extracted with $CH_2Cl_2$ (50 mL×3). The organic phases were combined, washed with 5% saline solution (50 mL×5), and dried over anhydrous $Na_2SO_4$. The dried organic phase was evaporated on a rotary evaporator to remove the solvent, and the resulting residue was purified and isolated by column chromatography to give products D and D'. The yields are calculated respectively, and the experimental conditions and the results are shown in Table 2.

TABLE 2

Experimental conditions and results

| Experiment No. | Solvent | Temperature (° C.) | MSCN | Yield of D (%) | Yield of D' (%) |
|---|---|---|---|---|---|
| 1 | DMF | 25 | KSCN | 0 | 90 |
| 2 | DMF | 40 | KSCN | 1 | 89 |
| 3 | DMF | 50 | KSCN | 1 | 91 |
| 4 | DMF | 60 | KSCN | 2 | 90 |
| 5 | DMF | 70 | KSCN | 3 | 87 |
| 6 | DMF | 80 | KSCN | 3 | 88 |
| 7 | DMF | 90 | KSCN | 14 | 64 |
| 8 | DMF | 100 | KSCN | 45 | 40 |
| 9 | DMF | 110 | KSCN | 78 | 12 |
| 10 | DMF | 120 | KSCN | 92 | 2 |
| 11 | DMF | 130 | KSCN | 93 | 2 |
| 12 | DMF | 140 | | 90 | 1 |
| 13 | DMF | reflux temperature of DMF* | KSCN | 90 | 2 |
| 14 | DMF | 120 | NaSCN | 92 | 3 |
| 15 | DMF | 140 | NaSCN | 91 | 1 |
| 16 | DMF | reflux temperature of DMF* | NaSCN | 91 | 1 |
| 17 | DMF | 120 | NH$_4$SCN | 90 | 2 |
| 18 | DMF | 140 | NH$_4$SCN | 90 | 2 |
| 19 | DMF | reflux temperature of DMF* | NH$_4$SCN | 91 | 1 |
| 20 | N,N-dimethyl acetamide (DMA) | 140 | KSCN | 85 | 1 |
| 21 | DMSO | 140 | KSCN | 87 | 1 |
| 22 | N-methyl pyrrolidone (NMP) | 140 | KSCN | 80 | 3 |
| 23 | hexamethyl phosphoramide (HMPA) | 140 | KSCN | 84 | 2 |
| 24 | MeOH | reflux temperature of MeOH* | KSCN | 0 | 65 |
| 25 | EtOH | reflux temperature of EtOH* | KSCN | 0 | 33 |
| 26 | acetone | reflux temperature of acetone* | KSCN | 1 | 61 |
| 27 | EtOAc | reflux temperature of EtOAc* | KSCN | 0 | 49 |
| 28 | MeCN | reflux temperature of MeCN* | KSCN | 0 | 64 |
| 29 | THF | reflux temperature of THF* | KSCN | 0 | 54 |

*Note:
the boiling point of DMF under a pressure of 760 mmHg is 153° C., but it is a common knowledge of those of ordinary skill in the art that under actual experimental conditions, the actual boiling temperature of DMF is affected by many factors (such as the altitude of experiment site and the types and concentrations of solutes dissolved in DMF) and may fluctuate around 153° C. Similarly, the reflux temperatures of several solvents described in the above table are also around their boiling points. The boiling point of MeOH is 65° C.; the boiling point of EtOH is 78° C.; the boiling point of acetone is 56.5° C.; the boiling point of EtOAc is 77° C.; the boiling point of MeCN is 81° C.; and the boiling point of THF is 65° C.

Conclusion: as can be seen from Table 2, in contrast to what recognized by those of ordinary skill in the art, the reaction between compound C' and a thiocyanate was very rapid and can be rapidly completed at room temperature. However, the distribution of the products is obviously temperature dependent. At a higher temperature, it tends to be produce D which is desired in the present invention, but at a lower temperature, the products are primarily isomer D'. The temperature at which D/D' tendency can be reversed is about 100° C. At the same time, the reaction proceeds well in an aprotic dipolar solvent such as DMF, DMA, DMSO, NMP, and HMPA, but does not proceeds well in other solvents.

Example 4 Synthetic Route of the Present Invention

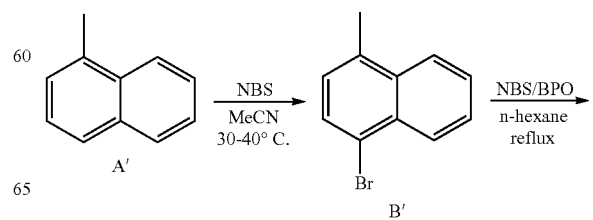

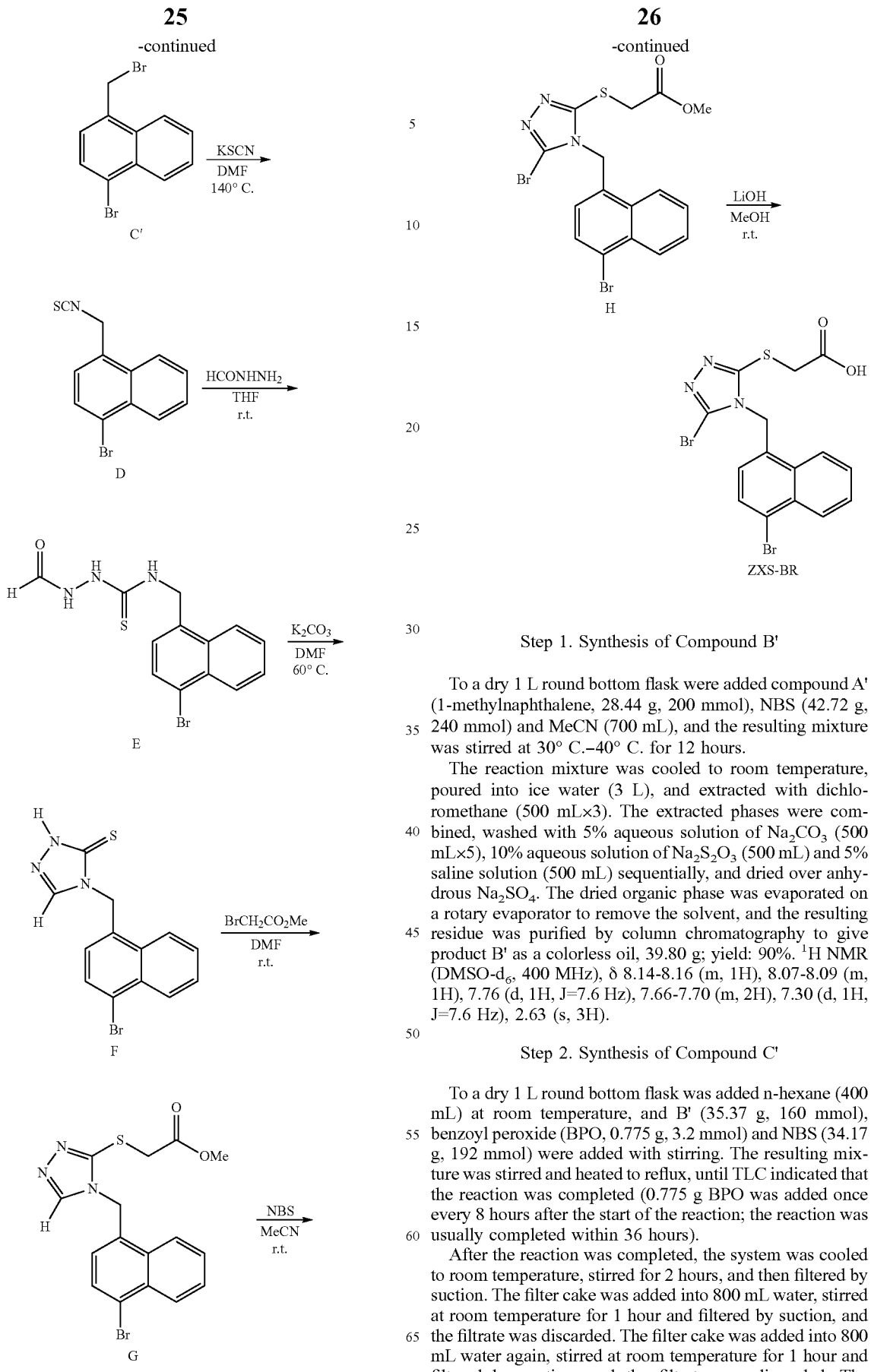

Step 1. Synthesis of Compound B'

To a dry 1 L round bottom flask were added compound A' (1-methylnaphthalene, 28.44 g, 200 mmol), NBS (42.72 g, 240 mmol) and MeCN (700 mL), and the resulting mixture was stirred at 30° C.–40° C. for 12 hours.

The reaction mixture was cooled to room temperature, poured into ice water (3 L), and extracted with dichloromethane (500 mL×3). The extracted phases were combined, washed with 5% aqueous solution of $Na_2CO_3$ (500 mL×5), 10% aqueous solution of $Na_2S_2O_3$ (500 mL) and 5% saline solution (500 mL) sequentially, and dried over anhydrous $Na_2SO_4$. The dried organic phase was evaporated on a rotary evaporator to remove the solvent, and the resulting residue was purified by column chromatography to give product B' as a colorless oil, 39.80 g; yield: 90%. $^1$H NMR (DMSO-$d_6$, 400 MHz), δ 8.14-8.16 (m, 1H), 8.07-8.09 (m, 1H), 7.76 (d, 1H, J=7.6 Hz), 7.66-7.70 (m, 2H), 7.30 (d, 1H, J=7.6 Hz), 2.63 (s, 3H).

Step 2. Synthesis of Compound C'

To a dry 1 L round bottom flask was added n-hexane (400 mL) at room temperature, and B' (35.37 g, 160 mmol), benzoyl peroxide (BPO, 0.775 g, 3.2 mmol) and NBS (34.17 g, 192 mmol) were added with stirring. The resulting mixture was stirred and heated to reflux, until TLC indicated that the reaction was completed (0.775 g BPO was added once every 8 hours after the start of the reaction; the reaction was usually completed within 36 hours).

After the reaction was completed, the system was cooled to room temperature, stirred for 2 hours, and then filtered by suction. The filter cake was added into 800 mL water, stirred at room temperature for 1 hour and filtered by suction, and the filtrate was discarded. The filter cake was added into 800 mL water again, stirred at room temperature for 1 hour and filtered by suction, and the filtrate was discarded. The resulting filter cake was pulped by stirring in 800 mL n-hexane for 2 hours and filtered by suction. The filter cake was dried to give a pure product of C' as a white solid, 34.56 g; yield: 72%; m.p.: 104.0-105.5° C. $^1$H NMR (DMSO-$d_6$, 400 MHz), δ 8.20-8.26 (m, 2H), 7.86 (d, 1H, J=8.0 Hz), 7.72-7.78 (m, 2H), 7.62 (d, 1H, J=7.6 Hz), 5.21 (s, 2H).

Step 3. Synthesis of Compound D

To a dry 1 L round bottom flask was added compound C' (30.00 g, 100 mmol), dissolved in dry DMF (300 mL), and then heated to 140° C. with stirring. KSCN (11.66 g, 120 mmol) was added in three portions within 1 minute. After the addition was completed, the reaction mixture was further stirred at 140° C. for 1 hour.

The reaction mixture was cooled to room temperature, then poured into stirring ice water (2000 mL), stirred and extracted with $CH_2Cl_2$ (300 mL×3). The organic phases were combined, washed with 5% saline solution (200 mL×5), and dried over anhydrous $Na_2SO_4$. The dried organic phase was evaporated on a rotary evaporator to remove the solvent, and the resulting residue was purified by column chromatography to give product D as a white solid, 25.59 g; yield: 92%; m.p.: 94.5-97.5° C. $^1$H NMR (DMSO-$d_6$, 400 MHz), δ 8.21-8.24 (m, 1H), 8.11-8.14 (m, 1H), 7.92 (d, 1H, J=7.6 Hz), 7.73-7.78 (m, 2H), 7.52 (d, 1H, J=8.0 Hz), 5.41 (s, 2H).

Step 4. Synthesis of Compound F

The above-described crude compound D (6.95 g, calculated as 25 mmol) was dissolved in THF (100 mL), and stirred at room temperature. Formylhydrazine (1.80 g, 30 mmol) was added, and then the stirring was continued overnight. At this point the reaction was detected for completion by TLC.

The reaction mixture was evaporated on a rotary evaporator to dryness, the resulting residue, i.e., a crude product of E, was dissolved in DMF (80 mL), and a solution made by solid $K_2CO_3$ (3.46 g, 25 mol) and water (10 mL) was added. The reaction mixture was stirred at 50° C. until the reaction was completed (usually 5 hours).

The reaction mixture was cooled to room temperature, poured into ice water (400 mL), stirred, adjusted with hydrochloric acid to pH=5-6, and extracted with $CH_2Cl_2$ (150 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product F as a white solid. $^1$H NMR showed that about 5% debromination by-product was contained therein. The crude F was crystallized twice with ethyl acetate to give a pure product of F, 6.96 g; yield: 87% (D→F); m.p.: 243-244° C. $^1$H NMR (DMSO-$d_6$, 400 MHz), δ 13.88 (brs, 1H), 8.37 (s, 1H), 8.22 (d, 2H, J=7.6 Hz), 7.90 (d, 1H, J=7.2 Hz), 7.72 (m, 2H), 7.18 (d, 1H, J=7.2 Hz), 5.61 (s, 2H).

Step 5. Synthesis of Compound G

Compound F (6.40 g, 20 mmol) was dissolved in DMF (100 mL) and stirred at room temperature, and solid $K_2CO_3$ (8.29 g, 60 mmol) and methyl bromoacetate (3.67 g, 24 mmol) were added. The resulting reaction mixture was stirred continuously at room temperature until the completion of the reaction was found by TLC determination (usually within 5 hours).

The reaction mixture was poured into ice water (400 mL), stirred, and extracted with $CH_2Cl_2$ (100 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product G as a white solid, 7.37 g; yield: 94%; m.p.: 112.5-114° C. $^1$H NMR (DMSO-$d_6$, 400 MHz), δ 8.67 (s, 1H), 8.22-8.25 (m, 1H), 8.15-8.17 (m, 1H), 7.88 (d, 1H, J=7.6 Hz), 7.72-7.79 (m, 2H), 6.92 (d, 1H, J=7.6 Hz), 5.72 (s, 2H), 4.07 (s, 2H), 3.62 (s, 3H).

Step 6. Synthesis of Compound H

Compound G (3.92 g, 10 mmol) was dissolved in acetonitrile (50 mL) and stirred at room temperature. NBS (2.14 g, 12 mmol) was added, and the stirring was continued at room temperature until the completion of the reaction was found by TLC determination (usually within 12 hours).

The reaction mixture was poured into ice water (200 mL), stirred, and extracted with $CH_2Cl_2$ (100 mL×3). The organic phases were combined, and washed with a saturated aqueous solution of $Na_2CO_3$ (100 mL×3) and 5% saline solution (200 mL) sequentially, and dried over anhydrous $Na_2SO_4$. The dried organic phase was evaporated on a rotary evaporator to remove the solvent, and the resulting residue was purified by column chromatography to give product H as a white solid, 3.49 g; m.p.: 141-143° C.; yield: 74%. $^1$H NMR (DMSO-$d_6$, 400 MHz), δ 8.21-8.26 (m, 2H), 7.84 (d, 1H, J=8.0 Hz), 7.76-7.82 (m, 2H), 6.49 (d, 1H, J=7.6 Hz), 5.74 (s, 2H), 4.08 (s, 2H), 3.61 (s, 3H).

Step 7. Synthesis of ZXS-BR

Compound H (3.30 g, 7 mmol) was added into methanol (50 mL) and stirred at room temperature. A solution made by $LiOH.H_2O$ (0.84 g, 20 mmol) and water (3 mL) was added, and then stirred at room temperature until the completion of the reaction was found by TLC determination (usually 2 hours).

The reaction mixture was poured into ice water (200 mL), stirred, adjusted with hydrochloric acid to pH=2-3, and extracted with $CH_2Cl_2$ (100 mL×4). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product ZXS-BR as a white solid, 2.82 g; yield: 88%; m.p.: 169.5-171.5° C. $^1$H NMR (DMSO-$d_6$, 400 MHz), δ 12.97 (brs, 1H), 8.22-8.26 (m, 2H), 7.83 (d, 1H, J=8.0 Hz), 7.76-7.81 (m, 2H), 6.51 (d, 1H, J=8.0 Hz), 5.73 (s, 2H), 4.01 (s, 2H).

Example 5 Synthetic Route of the Present Invention

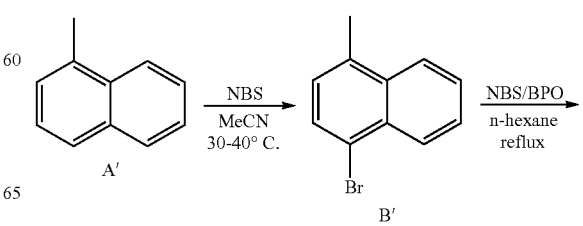

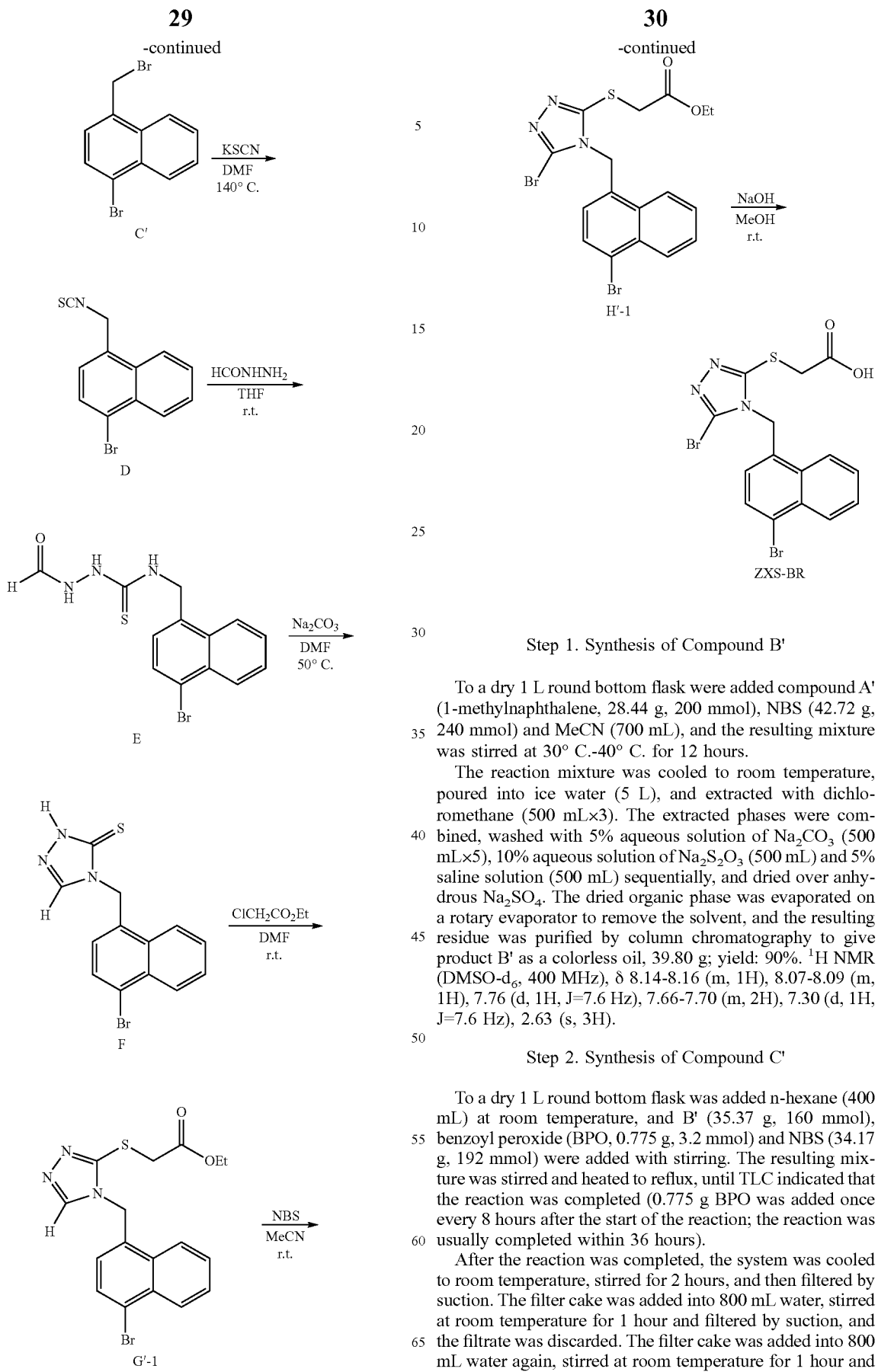

Step 1. Synthesis of Compound B'

To a dry 1 L round bottom flask were added compound A' (1-methylnaphthalene, 28.44 g, 200 mmol), NBS (42.72 g, 240 mmol) and MeCN (700 mL), and the resulting mixture was stirred at 30° C.-40° C. for 12 hours.

The reaction mixture was cooled to room temperature, poured into ice water (5 L), and extracted with dichloromethane (500 mL×3). The extracted phases were combined, washed with 5% aqueous solution of $Na_2CO_3$ (500 mL×5), 10% aqueous solution of $Na_2S_2O_3$ (500 mL) and 5% saline solution (500 mL) sequentially, and dried over anhydrous $Na_2SO_4$. The dried organic phase was evaporated on a rotary evaporator to remove the solvent, and the resulting residue was purified by column chromatography to give product B' as a colorless oil, 39.80 g; yield: 90%. $^1$H NMR (DMSO-$d_6$, 400 MHz), δ 8.14-8.16 (m, 1H), 8.07-8.09 (m, 1H), 7.76 (d, 1H, J=7.6 Hz), 7.66-7.70 (m, 2H), 7.30 (d, 1H, J=7.6 Hz), 2.63 (s, 3H).

Step 2. Synthesis of Compound C'

To a dry 1 L round bottom flask was added n-hexane (400 mL) at room temperature, and B' (35.37 g, 160 mmol), benzoyl peroxide (BPO, 0.775 g, 3.2 mmol) and NBS (34.17 g, 192 mmol) were added with stirring. The resulting mixture was stirred and heated to reflux, until TLC indicated that the reaction was completed (0.775 g BPO was added once every 8 hours after the start of the reaction; the reaction was usually completed within 36 hours).

After the reaction was completed, the system was cooled to room temperature, stirred for 2 hours, and then filtered by suction. The filter cake was added into 800 mL water, stirred at room temperature for 1 hour and filtered by suction, and the filtrate was discarded. The filter cake was added into 800 mL water again, stirred at room temperature for 1 hour and filtered by suction, and the filtrate was discarded. The resulting filter cake was pulped by stirring in 800 mL n-hexane for 2 hours and filtered by suction. The filter cake was dried to give a pure product of C' as a white solid, 34.56 g; yield: 72%; imp.: 104.0-105.5° C. $^1$H NMR (DMSO-$d_6$, 400 MHz), δ 8.20-8.26 (m, 2H), 7.86 (d, 1H, J=8.0 Hz), 7.72-7.78 (m, 2H), 7.62 (d, 1H, J=7.6 Hz), 5.21 (s, 2H).

Step 3. Synthesis of Compound D

To a dry 1 L round bottom flask was added compound C' (30.00 g, 100 mmol), dissolved in dry DMF (300 mL), and then heated to 140° C. with stirring. KSCN (11.66 g, 120 mmol) was added in three portions within 1 minute. After the addition was completed, the reaction mixture was further stirred at 140° C. for 1 hour.

The reaction mixture was cooled to room temperature, poured into stirring ice water (2000 mL), stirred and extracted with $CH_2Cl_2$ (300 mL×3). The organic phases were combined, washed with 5% saline solution (200 mL×5), and dried over anhydrous $Na_2SO_4$. The dried organic phase was evaporated on a rotary evaporator to remove the solvent, and the resulting residue was purified by column chromatography to give product D as a white solid, 25.59 g; yield: 92%; m.p.: 94.5-97.5° C. $^1$H NMR (DMSO-$d_6$, 400 MHz), δ 8.21-8.24 (m, 1H), 8.11-8.14 (m, 1H), 7.92 (d, 1H, J=7.6 Hz), 7.73-7.78 (m, 2H), 7.52 (d, 1H, J=8.0 Hz), 5.41 (s, 2H).

Step 4. Synthesis of Compound F

The above-described crude compound D (6.95 g, calculated as 25 mmol) was dissolved in THF (100 mL), and stirred at room temperature. Formylhydrazine (1.80 g, 30 mmol) was added, and then the stirring was continued overnight. At this point the reaction was detected for completion by TLC.

The reaction mixture was evaporated on a rotary evaporator to dryness, the resulting residue, i.e., a crude product of E, was dissolved in DMF (80 mL), and a mixture made by solid $Na_2CO_3$ (2.65 g, 25 mol) and water (10 mL) was added. The reaction mixture was stirred at 50° C. until the reaction was completed (usually 5 hours).

The reaction mixture was cooled to room temperature, poured into ice water (400 mL), stirred, adjusted with hydrochloric acid to pH=5-6, and extracted with $CH_2Cl_2$ (150 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product F as a white solid. $^1$H NMR showed that about 5% debromination by-product was contained therein. The crude F was crystallized twice with ethyl acetate to give a pure product of F, 6.80 g; yield: 85% (D→F); m.p.: 243-244° C. $^1$H NMR (DMSO-$d_6$, 400 MHz), δ 13.88 (brs, 1H), 8.37 (s, 1H), 8.22 (d, 2H, J=7.6 Hz), 7.90 (d, 1H, J=7.2 Hz), 7.72 (m, 2H), 7.18 (d, 1H, J=7.2 Hz), 5.61 (s, 2H).

Step 5. Synthesis of Compound G'-1

Compound F (6.40 g, 20 mmol) was dissolved in DMF (100 mL) and stirred at room temperature, and solid $K_2CO_3$ (8.29 g, 60 mmol) and ethyl chloroacetate (2.94 g, 24 mmol) were added. The resulting reaction mixture was stirred continuously at room temperature until the completion of the reaction was found by TLC determination (usually within 10 hours).

The reaction mixture was poured into ice water (400 mL), stirred, and extracted with $CH_2Cl_2$ (100 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product G'-1 as a white solid, 7.72 g; yield: 95%. ESI-MS, m/z=406, 408 ([M+H]$^+$).

Step 6. Synthesis of Compound H'-1

Compound G'-1 (4.06 g, 10 mmol) was dissolved in acetonitrile (50 mL) and stirred at room temperature. NBS (2.14 g, 12 mmol) was added, and the stirring was continued at room temperature until the completion of the reaction was found by TLC determination (usually within 12 hours).

The reaction mixture was poured into ice water (200 mL), stirred, and extracted with $CH_2Cl_2$ (100 mL×3). The organic phases were combined, and washed with a saturated $Na_2CO_3$ solution (100 mL×3) and 5% saline solution (200 mL) sequentially, and dried over anhydrous $Na_2SO_4$. The dried organic phase was evaporated on a rotary evaporator to remove the solvent, and the resulting residue was purified by column chromatography to give product H'-1 as a white solid, 3.69 g; yield: 76%. ESI-MS, m/z=486 ([M+H]$^+$).

Step 7. Synthesis of ZXS-BR

Compound H'-1 (3.40 g, 7 mmol) was added into methanol (40 mL) and stirred at room temperature. A solution made by NaOH (0.8 g, 20 mmol) and water (1 mL) was added, and then stirred at room temperature until the completion of the reaction was found by TLC determination (usually 2 hours).

The reaction mixture was poured into ice water (200 mL), stirred, adjusted with hydrochloric acid to pH=2-3, and extracted with $CH_2Cl_2$ (100 mL×4). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product ZXS-BR as a white solid, 2.82 g; yield: 88%; m.p.: 169.5-171.5° C. $^1$H NMR (DMSO-$d_6$, 400 MHz), δ 12.97 (brs, 1H), 8.22-8.26 (m, 2H), 7.83 (d, 1H, J=8.0 Hz), 7.76-7.81 (m, 2H), 6.51 (d, 1H, J=8.0 Hz), 5.73 (s, 2H), 4.01 (s, 2H).

Example 6 Synthetic Route of the Present Invention

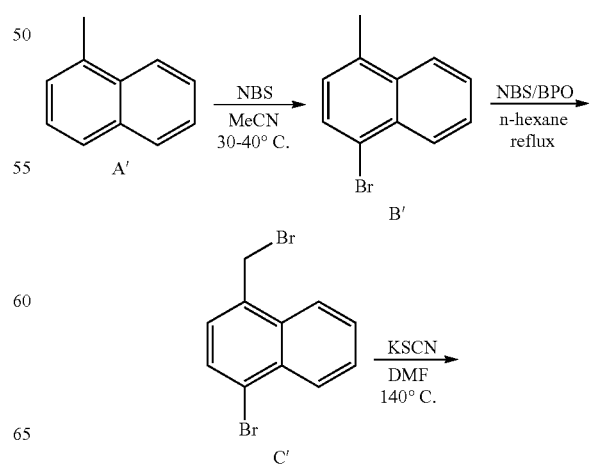

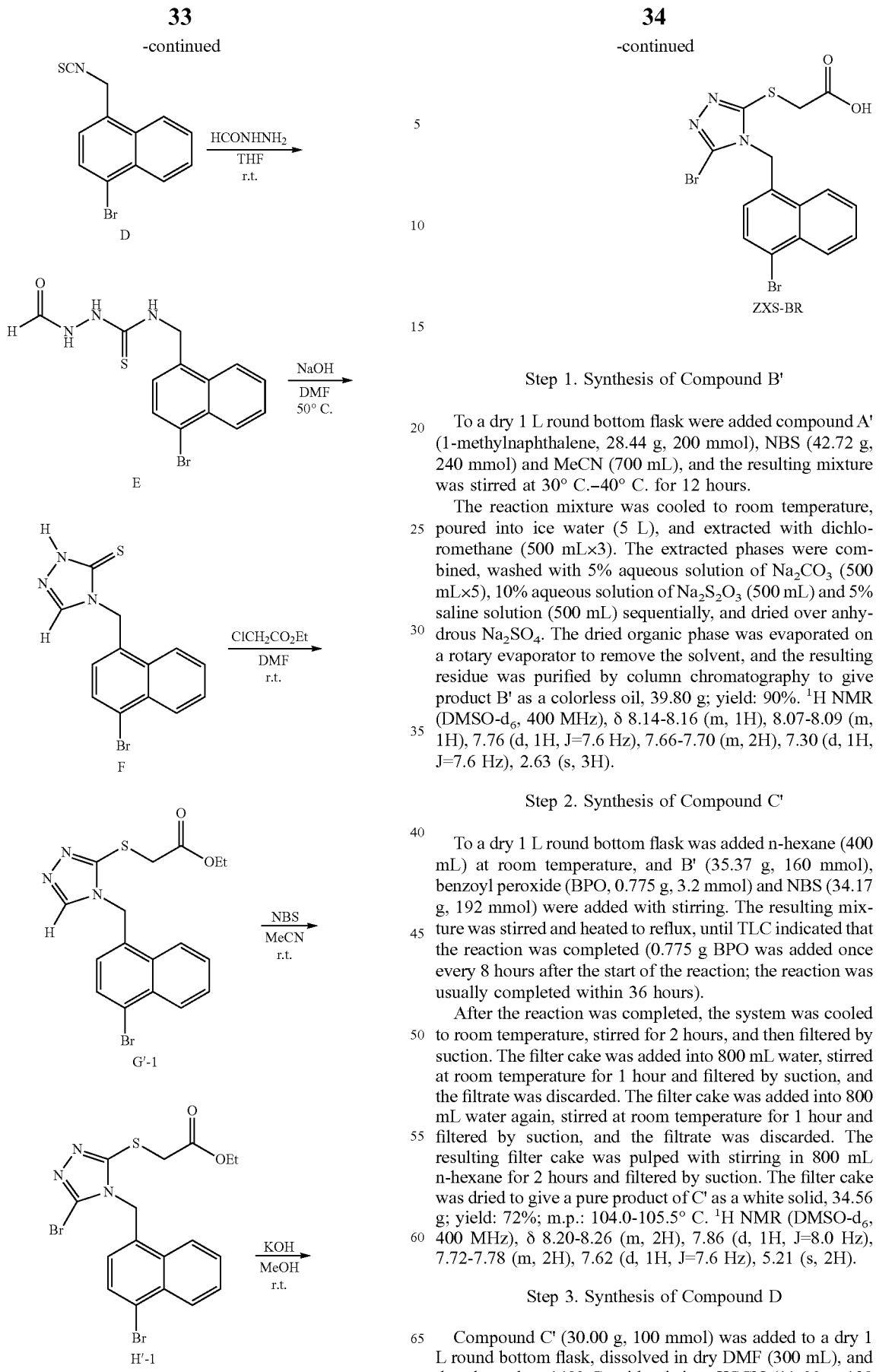

Step 1. Synthesis of Compound B'

To a dry 1 L round bottom flask were added compound A' (1-methylnaphthalene, 28.44 g, 200 mmol), NBS (42.72 g, 240 mmol) and MeCN (700 mL), and the resulting mixture was stirred at 30° C.–40° C. for 12 hours.

The reaction mixture was cooled to room temperature, poured into ice water (5 L), and extracted with dichloromethane (500 mL×3). The extracted phases were combined, washed with 5% aqueous solution of $Na_2CO_3$ (500 mL×5), 10% aqueous solution of $Na_2S_2O_3$ (500 mL) and 5% saline solution (500 mL) sequentially, and dried over anhydrous $Na_2SO_4$. The dried organic phase was evaporated on a rotary evaporator to remove the solvent, and the resulting residue was purified by column chromatography to give product B' as a colorless oil, 39.80 g; yield: 90%. $^1$H NMR (DMSO-$d_6$, 400 MHz), δ 8.14-8.16 (m, 1H), 8.07-8.09 (m, 1H), 7.76 (d, 1H, J=7.6 Hz), 7.66-7.70 (m, 2H), 7.30 (d, 1H, J=7.6 Hz), 2.63 (s, 3H).

Step 2. Synthesis of Compound C'

To a dry 1 L round bottom flask was added n-hexane (400 mL) at room temperature, and B' (35.37 g, 160 mmol), benzoyl peroxide (BPO, 0.775 g, 3.2 mmol) and NBS (34.17 g, 192 mmol) were added with stirring. The resulting mixture was stirred and heated to reflux, until TLC indicated that the reaction was completed (0.775 g BPO was added once every 8 hours after the start of the reaction; the reaction was usually completed within 36 hours).

After the reaction was completed, the system was cooled to room temperature, stirred for 2 hours, and then filtered by suction. The filter cake was added into 800 mL water, stirred at room temperature for 1 hour and filtered by suction, and the filtrate was discarded. The filter cake was added into 800 mL water again, stirred at room temperature for 1 hour and filtered by suction, and the filtrate was discarded. The resulting filter cake was pulped with stirring in 800 mL n-hexane for 2 hours and filtered by suction. The filter cake was dried to give a pure product of C' as a white solid, 34.56 g; yield: 72%; m.p.: 104.0-105.5° C. $^1$H NMR (DMSO-$d_6$, 400 MHz), δ 8.20-8.26 (m, 2H), 7.86 (d, 1H, J=8.0 Hz), 7.72-7.78 (m, 2H), 7.62 (d, 1H, J=7.6 Hz), 5.21 (s, 2H).

Step 3. Synthesis of Compound D

Compound C' (30.00 g, 100 mmol) was added to a dry 1 L round bottom flask, dissolved in dry DMF (300 mL), and then heated to 140° C. with stirring. KSCN (11.66 g, 120 mmol) was added in three portions within 1 minute. After the addition was completed, the reaction mixture was further stirred at 140° C. for 1 hour.

The reaction mixture was cooled to room temperature, then poured into stirring ice water (2000 mL), stirred and extracted with $CH_2Cl_2$ (300 mL×3). The organic phases were combined, washed with 5% saline solution (200 mL×5), and dried over anhydrous $Na_2SO_4$. The dried organic phase was evaporated on a rotary evaporator to remove the solvent, and the resulting residue was purified by column chromatography to give product D as a white solid, 25.59 g; yield: 92%; m.p.: 94.5-97.5° C. $^1$H NMR (DMSO-$d_6$, 400 MHz), δ 8.21-8.24 (m, 1H), 8.11-8.14 (m, 1H), 7.92 (d, 1H, J=7.6 Hz), 7.73-7.78 (m, 2H), 7.52 (d, 1H, J=8.0 Hz), 5.41 (s, 2H).

Step 4. Synthesis of Compound F

The above-described crude compound D (6.95 g, calculated as 25 mmol) was dissolved in THF (100 mL), and stirred at room temperature. Formylhydrazine (1.80 g, 30 mmol) was added, and then the stirring was continued overnight. At this point the reaction was detected for completion by TLC.

The reaction mixture was evaporated on a rotary evaporator to dryness, the resulting residue, i.e., a crude product of E, was dissolved in DMF (80 mL), and a mixture made by solid NaOH (1.00 g, 25 mol) and water (5 mL) was added. The reaction mixture was stirred at 50° C. until the reaction was completed (usually 5 hours).

The reaction mixture was cooled to room temperature, poured into ice water (400 mL), stirred, adjusted with hydrochloric acid to pH=5-6, and extracted with $CH_2Cl_2$ (150 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product F as a white solid. $^1$H NMR showed that about 5% debromination by-product was contained therein. The crude F was crystallized twice with ethyl acetate to give a pure product of F, 6.64 g; yield: 83% (D→F); m.p.: 243-244° C. $^1$H NMR (DMSO-$d_6$, 400 MHz), δ 13.88 (brs, 1H), 8.37 (s, 1H), 8.22 (d, 2H, J=7.6 Hz), 7.90 (d, 1H, J=7.2 Hz), 7.72 (m, 2H), 7.18 (d, 1H, J=7.2 Hz), 5.61 (s, 2H).

Step 5. Synthesis of Compound G'-1

Compound F (6.40 g, 20 mmol) was dissolved in DMF (100 mL) and stirred at room temperature, and solid $K_2CO_3$ (8.29 g, 60 mmol) and ethyl chloroacetate (2.94 g, 24 mmol) were added. The resulting reaction mixture was stirred continuously at room temperature until the completion of the reaction was found by TLC determination (usually within 10 hours).

The reaction mixture was poured into ice water (400 mL), stirred, and extracted with $CH_2Cl_2$ (100 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product G'-1 as a white solid, 7.72 g; yield: 95%. ESI-MS, m/z=406, 408 ([M+H]$^+$).

Step 6. Synthesis of Compound H'-1

Compound G'-1 (4.06 g, 10 mmol) was dissolved in acetonitrile (50 mL) and stirred at room temperature. NBS (2.14 g, 12 mmol) was added, and the stirring was continued at room temperature until the completion of the reaction was found by TLC determination (usually within 12 hours).

The reaction mixture was poured into ice water (200 mL), stirred, and extracted with $CH_2Cl_2$ (100 mL×3). The organic phases were combined, and washed with a saturated $Na_2CO_3$ solution (100 mL×3) and 5% saline solution (200 mL) sequentially, and dried over anhydrous $Na_2SO_4$. The dried organic phase was evaporated on a rotary evaporator to remove the solvent, and the resulting residue was purified by column chromatography to give product H'-1 as a white solid, 3.69 g; yield: 76%. ESI-MS, m/z=486 ([M+H]$^+$).

Step 7. Synthesis of ZXS-BR

Compound H'-1 (3.40 g, 7 mmol) was added into methanol (40 mL) and stirred at room temperature. A solution made by KOH (1.12 g, 20 mmol) and water (1 mL) was added, and then stirred at room temperature until the completion of the reaction was found by TLC determination (usually 2 hours).

The reaction mixture was poured into ice water (200 mL), stirred, adjusted with hydrochloric acid to pH=2-3, and extracted with $CH_2Cl_2$ (100 mL×4). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give product ZXS-BR as a white solid, 2.82 g; yield: 88%; m.p.: 169.5-171.5° C. $^1$H NMR (DMSO-$d_6$, 400 MHz), δ 12.97 (brs, 1H), 8.22-8.26 (m, 2H), 7.83 (d, 1H, J=8.0 Hz), 7.76-7.81 (m, 2H), 6.51 (d, 1H, J=8.0 Hz), 5.73 (s, 2H), 4.01 (s, 2H).

The invention claimed is:
1. A method for preparing a urate transporter 1 inhibitor, 2-((5-bromo-4-((4-bromonaphthalen-1-yl)methyl)-4H-1,2, 4-triazol-3-yl)thio) acetic acid represented by the formula ZXS-BR, comprising the following steps:
  1) performing a bromination reaction of N-bromosuccinimide and starting material A' to obtain product B';
  2) reacting product B' obtained from step 1) with N-bromosuccinimide in the presence of a radical initiator to obtain product C';
  3) reacting product C' obtained from step 2) with a thiocyanate at a temperature no lower than 100° C. to obtain product D;
  4) reacting product D obtained from step 3) with formylhydrazine to obtain product E;
  5) performing a ring closure reaction of product E obtained from step 4) in the presence of a base to obtain product F;
  6) reacting product F obtained from step 5) with $XCH_2CO_2R$ in the presence of a base to obtain product G';
  wherein, X is selected from Cl, Br or I, and R is selected from $C_1$-$C_{10}$ alkyl or $C_3$-$C_6$ cycloalkyl;
  7) reacting product G' obtained from step 6) with N-bromosuccinimide to obtain product H'; and
  8) hydrolyzing product H' obtained from step 7) in the presence of a base to obtain ZXS-BR;
  wherein, the formulas A', B', C', D, E, F, G', H' and ZXS-BR represent the following compounds, respectively:

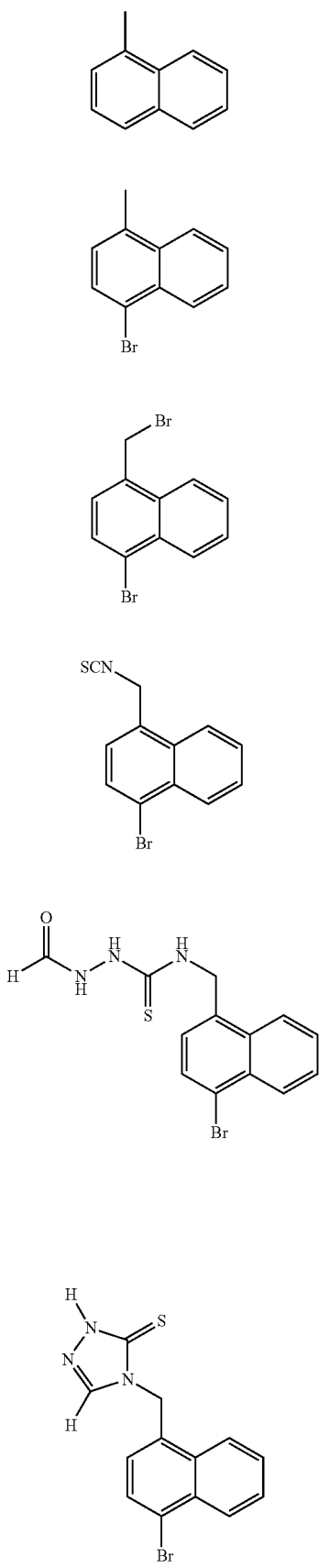

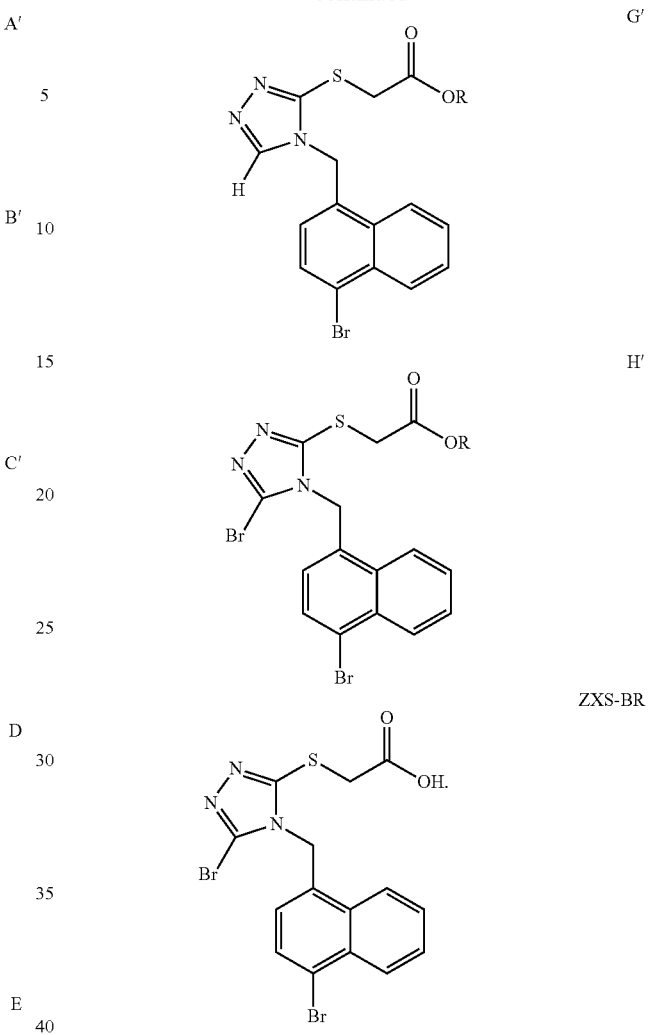

2. The method of claim 1, wherein the reaction in step 1) is conducted in acetonitrile, and the reaction temperature is from 30 to 40° C.

3. The method of claim 1, wherein in step 2), the radical initiator is benzoyl peroxide or azodiisobutyronitrile.

4. The method of claim 1, wherein the reaction in step 2) is conducted in a solvent of the reaction selected from $C_5$-$C_{17}$ alkane or cycloalkane, or petroleum ether fraction obtained by fractionation at 30-150° C.

5. The method of claim 4, wherein $C_5$-$C_{17}$ alkane or cycloalkane is n-pentane, cyclopentane, n-hexane, cyclohexane, or n-heptane.

6. The method of claim 4, wherein in step 2), the temperature of the reaction is the reflux temperature of the solvent.

7. The method of claim 1, wherein in step 2), the temperature of the reaction is from 36° C. to 120° C.

8. The method of claim 1, wherein in step 3), the thiocyanate is a thiocyanate of alkali metal, alkaline earth metal or ammonium.

9. The method of claim 1, wherein in step 3), the thiocyanate is sodium thiocyanate, potassium thiocyanate or ammonium thiocyanate.

10. The method of claim 1, wherein in step 3), the temperature of the reaction is from 120° C. to 140° C.

11. The method of claim 1, wherein the reaction in step 3) is conducted in an aprotic dipolar solvent.

12. The method of claim 11, wherein the aprotic dipolar solvent is selected from dimethylformamide, N,N-dimethylacetamide, dimethyl sulfoxide, N-methylpyrrolidone, or hexamethylphosphoramide.

13. The method of claim 1, wherein in step 3), the temperature of the reaction is from 100° C. to the reflux temperature of the solvent.

14. The method of claim 1, wherein the reaction in step 4) is conducted in tetrahydrofuran.

15. The method of claim 1, wherein in step 5), the base is an alkali metal carbonate or an alkali metal hydroxide.

16. The method of claim 1, wherein in step 5), the base is $Na_2CO_3$, $K_2CO_3$, NaOH or KOH.

17. The method of claim 1, wherein in step 6), R is selected from $C_1$-$C_4$ alkyl.

18. The method of claim 1, wherein in step 6), R is selected from methyl or ethyl.

19. The method of claim 1, wherein in step 8), the base is selected from an alkali metal hydroxide.

20. The method of claim 1, wherein in step 8), the base is selected from LiOH, NaOH or KOH.

21. The method of claim 1, wherein the method comprises the following steps:
   1) performing a bromination reaction of N-bromosuccinimide and starting material A' in acetonitrile as a solvent at a temperature of 30-40° C. to obtain product B';
   2) heating product B' obtained from step 1), N-bromosuccinimide and benzoyl peroxide in n-hexane to reflux to obtain product C';
   3) reacting product C' obtained from step 2) with potassium thiocyanate in dimethylformamide as a solvent at a temperature of 140° C. to obtain product D;
   4) reacting product D obtained from step 3) with formylhydrazine in tetrahydrofuran as a solvent at room temperature to obtain product E;
   5) performing a ring closure reaction of product E obtained from step 4) with a base to obtain product F;
   6) reacting product F obtained from step 5) with $XCH_2CO_2R$ in the presence of a base to obtain product G';
   wherein, X is selected from Cl, Br or I, and R is selected from $C_1$-$C_{10}$ alkyl or $C_3$-$C_6$ cycloalkyl;
   7) reacting product G' obtained from step 6) with N-bromosuccinimide to obtain product H'; and
   8) hydrolyzing product H' obtained from step 7) with a base to obtain ZXS-BR.

22. The method of claim 21, wherein in step 5), the base is an alkali metal carbonate or an alkali metal hydroxide.

23. The method of claim 21, wherein in step 5), the base is $Na_2CO_3$, $K_2CO_3$, NaOH or KOH.

24. The method of claim 21, wherein in step 6), R is selected from $C_1$-$C_4$ alkyl.

25. The method of claim 21, wherein in step 6), R is selected from methyl or ethyl.

26. The method of claim 21, wherein in step 8), the base is an alkali metal hydroxide.

27. The method of claim 21, wherein in step 8), the base is LiOH, NaOH or KOH.

28. A compound represented by the following formula H' or G' respectively:

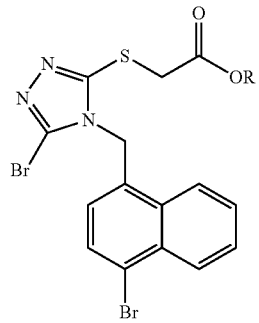

H'

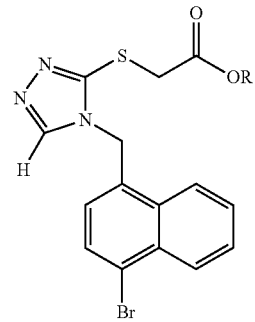

G' wherein, R is selected from $C_1$-$C_{10}$ alkyl or $C_3$-$C_6$ cycloalkyl.

29. The compound of claim 28, wherein R is selected from $C_1$-$C_4$ alkyl.

30. The compound of claim 28, wherein R is selected from methyl or ethyl.

31. A compound represented by the following formula D, E or F respectively:

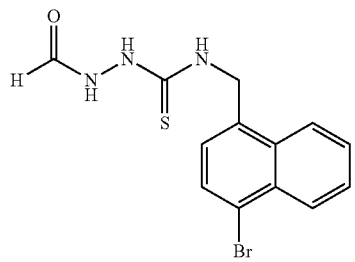

E

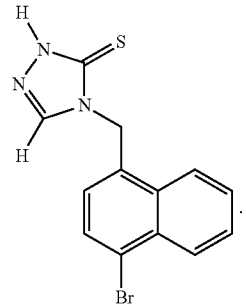

F

\* \* \* \* \*